US008425926B2

(12) United States Patent
Qiu et al.

(10) Patent No.: US 8,425,926 B2
(45) Date of Patent: Apr. 23, 2013

(54) ANTIMICROBIAL MEDICAL DEVICES

(76) Inventors: Yongxing Qiu, Duluth, GA (US); John Martin Lally, Lilburn, GA (US)

(*) Notice: Subject to any disclaimer, the term of this patent is extended or adjusted under 35 U.S.C. 154(b) by 2245 days.

(21) Appl. No.: 10/891,407

(22) Filed: Jul. 14, 2004

(65) Prior Publication Data
US 2005/0013842 A1    Jan. 20, 2005

Related U.S. Application Data

(60) Provisional application No. 60/487,780, filed on Jul. 16, 2003.

(51) Int. Cl.
*A61F 2/00* (2006.01)
(52) U.S. Cl.
USPC ........................................................ 424/423
(58) Field of Classification Search ................. None
See application file for complete search history.

(56) References Cited

U.S. PATENT DOCUMENTS

| | | | |
|---|---|---|---|
| 3,591,329 A | 7/1971 | Chromecek et al. .......... 21/61 |
| 4,131,696 A | 12/1978 | Covington et al. .......... 427/164 |
| 4,273,734 A | 6/1981 | Seiderman .................... 264/1.1 |
| 4,286,957 A | 9/1981 | Le Naour-Sene ................ 8/471 |
| 4,408,845 A | 10/1983 | Seiderman .................... 351/160 |
| 4,473,550 A | 9/1984 | Rosenbaum et al. ........... 424/94 |
| 4,499,077 A | 2/1985 | Stockel et al. ............... 424/149 |
| 4,592,920 A | 6/1986 | Murtfeldt .......................... 427/2 |
| 4,634,449 A | 1/1987 | Jenkins ............................ 8/507 |
| 4,654,208 A | 3/1987 | Stockel et al. .................. 424/78 |
| 4,666,640 A | 5/1987 | Neefe ............................. 264/2.1 |
| 4,677,143 A | 6/1987 | Laurin et al. ................... 523/122 |
| 4,681,412 A | 7/1987 | Lemelson ..................... 351/162 |
| 4,707,236 A | 11/1987 | Borowsky .................. 204/182.8 |
| 4,784,991 A | 11/1988 | Nimrod et al. ................... 514/62 |
| 4,849,223 A | 7/1989 | Pratt et al. ..................... 424/409 |
| 4,933,178 A | 6/1990 | Capelli ............................ 424/78 |
| 4,979,985 A | 12/1990 | Tosun |
| 5,011,602 A | 4/1991 | Totani .......................... 210/484 |
| 5,019,096 A | 5/1991 | Fox, Jr. et al. ................... 623/1 |
| 5,213,801 A | 5/1993 | Sakuma et al. ............... 424/429 |
| 5,314,980 A | 5/1994 | Morrison et al. .............. 528/19 |
| 5,320,908 A | 6/1994 | Sodervall et al. ............. 428/461 |
| 5,328,954 A | 7/1994 | Sarangapani ................. 524/589 |
| 5,340,583 A | 8/1994 | Dziabo et al. ................. 424/412 |
| 5,391,669 A | 2/1995 | Sule et al. ...................... 526/265 |
| 5,395,651 A | 3/1995 | Sodervall et al. ............. 427/304 |
| 5,395,697 A | 3/1995 | Morrison ....................... 428/412 |
| 5,462,644 A | 10/1995 | Woodson ...................... 204/131 |
| 5,490,938 A | 2/1996 | Sawan et al. ................... 210/651 |
| 5,494,756 A | 2/1996 | Siegel ............................ 428/447 |
| 5,515,117 A | 5/1996 | Dziabo et al. ................. 351/160 |
| 5,681,468 A | 10/1997 | Sawan et al. .............. 210/500.25 |
| 5,718,862 A | 2/1998 | Thompson .................... 264/296 |
| 5,747,178 A | 5/1998 | Sodervall et al. ............. 428/624 |
| 5,760,100 A * | 6/1998 | Nicolson et al. .............. 523/106 |
| 5,817,325 A | 10/1998 | Sawan et al. ................. 424/411 |
| 5,848,995 A | 12/1998 | Wader .......................... 604/265 |
| 5,849,311 A | 12/1998 | Sawan et al. ................. 424/406 |
| 5,869,073 A | 2/1999 | Sawan et al. ................. 424/406 |
| 5,965,204 A | 10/1999 | Sodervall et al. ............. 427/304 |
| 6,030,632 A | 2/2000 | Sawan et al. ................. 424/405 |
| 6,126,931 A | 10/2000 | Sawan et al. ............... 424/78.09 |
| 6,224,983 B1 | 5/2001 | Sodervall et al. ............. 428/461 |
| 6,264,936 B1 | 7/2001 | Sawan et al. ............... 424/78.26 |
| 6,267,782 B1 * | 7/2001 | Ogle et al. ....................... 623/1.1 |
| 6,312,713 B1 | 11/2001 | Korol et al. .................... 424/443 |
| 6,318,549 B1 | 11/2001 | Bougamont et al. ........... 206/5.1 |
| 6,350,251 B1 | 2/2002 | Prosl et al. ........................ 604/93 |
| 6,440,405 B1 | 8/2002 | Cooper et al. .............. 424/78.17 |
| 6,516,633 B1 | 2/2003 | Erskine et al. .................. 65/21.1 |
| 6,605,751 B1 * | 8/2003 | Gibbins et al. ................... 602/41 |
| 6,843,784 B2 | 1/2005 | Modak et al. .................. 604/265 |
| 2001/0044482 A1 * | 11/2001 | Hu et al. ........................ 523/106 |
| 2002/0119207 A1 | 8/2002 | Baker, Jr. et al. ............. 424/750 |
| 2002/0156170 A1 | 10/2002 | Border et al. .................. 524/433 |
| 2002/0197299 A1 * | 12/2002 | Vanderlaan et al. .......... 424/429 |
| 2003/0044447 A1 * | 3/2003 | Zanini et al. .................. 424/429 |
| 2003/0049300 A1 * | 3/2003 | Terry ............................. 424/423 |
| 2003/0095230 A1 | 5/2003 | Neely et al. ................... 351/159 |

FOREIGN PATENT DOCUMENTS

| | | |
|---|---|---|
| DE | 3026258 | 1/1982 |
| EP | 0 272 101 A2 | 12/1987 |
| EP | 0 272 101 A3 | 12/1987 |
| EP | 0 309 154 A2 | 9/1988 |
| EP | 0 309 154 A3 | 9/1988 |
| EP | 0 487 994 | 11/1991 |
| EP | 0 611 357 | 10/1992 |

(Continued)

OTHER PUBLICATIONS

Abstract Database WPI, Section Ch., Week 200353, Derwent Publications Ltd., London, GB; AN 2003-565724, XP002304948, & KR 2003 031 090 A (IHN K J), Apr. 18, 2003, abstract.
Abstract Database WPI, Section Ch., Week 200353, Derwent Publications Ltd., London, GB; AN 2003-565723, XP002268629, & KR 2003 031 089 A (IHN K J), Apr. 18, 2003, abstract.
Standard European Search Report, Jan. 2004.
International Search Report and Written Opinion, Jan. 2004.
Rohline, O., "Plastics in Medicine" V.53(3) 54-55, 2002.
Karlov, Khlusov, Pontak, Ignatov, Ivin, Zinatulina, "Adhesion of *Staphylococcus aureus* to Implants with Different Physicochemical Characteristics", 2002, 277-280.
Written Opinion of the International Searching Authority, Jan. 2004.
Wolf, JAMA, 130(5): 273-276 (1946).
Zhang, et al., Journal of Solid State Chemistry 121: 105-110 (1996).
Kopeikin & Panarin, Doklady Chemistry, 380, Nos. 4-6: 277-279 (2001).
Hybrids of Silver Nanoparticles with Amphiphilic Hyperbranched Macromolecules Exhibiting Antimicrobial Properties, Cyril Aymonier, et al., The Royal Society of Chemistry 2002, 2002, pp. 3018-3019.

(Continued)

*Primary Examiner* — Scott Long
*Assistant Examiner* — Sarah Alawadi
(74) *Attorney, Agent, or Firm* — Sheng-Hsin Hu; Jian Zhou

(57) ABSTRACT

The present invention provides methods for making an antimicrobial medical device, preferably an antimicrobial ophthalmic device, more preferably an antimicrobial extended-wear contact lens, which contains silver nano-particles distributed uniformly therein. The antimicrobial medical device can exhibit antimicrobial activity over an extended period of time.

17 Claims, No Drawings

FOREIGN PATENT DOCUMENTS

| | | | |
|---|---|---|---|
| EP | 0 903 389 | | 6/1997 |
| EP | 0 885 932 A2 | | 6/1998 |
| EP | 0 885 932 A3 | | 6/1998 |
| EP | 1 050 314 | | 5/2000 |
| GB | 2 202 962 | * | 3/1988 |
| GB | 2 202 962 | | 10/1988 |
| JP | 4-76518 | | 3/1992 |
| JP | 5-269181 | | 10/1993 |
| JP | 5-293090 | | 11/1993 |
| JP | 5-341240 | | 12/1993 |
| JP | 6-181970 | | 7/1994 |
| JP | 7-270726 | | 10/1995 |
| KR | 10-2004-0089035 | | 10/2004 |
| RU | 2058328 | | 4/1996 |
| WO | WO 87/05517 | | 9/1987 |
| WO | WO 87/05712 | | 9/1987 |
| WO | WO 94/27170 | | 11/1994 |
| WO | WO 95/18637 | | 7/1995 |
| WO | WO 9731709 | | 9/1997 |
| WO | WO 98/18330 | | 5/1998 |
| WO | WO 98/41579 | | 9/1998 |
| WO | WO 99/16390 | | 4/1999 |
| WO | WO 00/16815 | | 3/2000 |
| WO | WO 00/38552 | | 7/2000 |
| WO | WO 00/65915 | | 11/2000 |
| WO | WO 01/24839 | | 4/2001 |
| WO | WO 01/43788 | | 6/2001 |
| WO | WO 02/18003 | | 3/2002 |
| WO | WO 02/62402 | | 5/2002 |
| WO | WO 02/49683 | | 6/2002 |
| WO | WO 02/057837 | | 7/2002 |
| WO | WO 02/062402 | | 8/2002 |
| WO | WO 03/011351 | | 2/2003 |
| WO | WO 03/016217 | | 2/2003 |

OTHER PUBLICATIONS

Antimicrobial Efficacy of a Silver Layer on Hydrogel Lenses, S. Nissen, et al, Ophthalmologe, 7:640-643, 2000 (abstract).
Silver-Based Crystalline Nanoparticles, Microbially Fabricated, Tanja Klaus, et al PNAS, Nov. 23, 1999, vol. 96, No. 24, pp. 13611-13614.
Hydogenous and Exogenous Ocular and Systemic Silver Deposition, W. H. Spencer, et al.,Society UK 1980, 100,171.
Formulation and Stabilization of Silver Nanoparticles through Reduction by N, N.—Dimethylformamide, Isabel Pastoriza-Santos, et al., 1999 American Chemical Society, Jan. 15, 1999, pp. 948-951.
Evaluation of "Bacteriostatic" contact Lenses, Thomas Chalkley, et al, pp. 866-869, May 1996.
Search Report #1, Dec. 2003.
Search Report #2, Dec. 18, 2003.
Search Report #3, Dec. 21, 2003.
Search Report #4, Feb. 25, 2003.
Search Report #5, Mar. 24, 2003.
Search Report #6, Mar. 24, 2003.
Search Report #7, Feb. 25, 2003.
Search Report #8, Jan. 29, 2003.
Search Report #9, Jan. 29, 2003.
Search Report #10, Jan. 29, 2003.
Search Report #11.
Search Report #12, Feb. 21, 2003.
Search Report #13, Feb. 21, 2003.
Search Report #14, Feb. 21, 2003.

* cited by examiner

ANTIMICROBIAL MEDICAL DEVICES

This application claims the benefit under 35 USC §119 (e) of U.S. provisional application No. 60/487,780 filed Jul. 16, 2003, incorporated by reference in its entirety.

The present invention generally relates to methods for making an antimicrobial medical device having silver nanoparticles distributed therein and to an antimicrobial medical device made therefrom.

BACKGROUND

Contact lenses are often exposed to one or more microorganisms during wear, storage and handling. They can provide surfaces onto which the microorganisms can adhere and then proliferate to form a colony. Microbial adherence to and colonization of contact lenses may enable microorganisms to proliferate and to be retained on the ocular surface for prolonged periods and thereby may cause infection or other deleterious effects on the ocular health of the eye in which the lens is used. Therefore, it is desirous to make various efforts to minimize and/or eliminate the potential for microorganism adhesion to and colonization of contact lenses.

Many attempts have been made to develop antimicrobial medical devices. Two approaches have been proposed. One approach is to incorporate antimicrobial compounds into a polymeric composition for molding a contact lens. For example, Chalkley et al. in Am. J. Ophthalmology 1966, 61:866-869, disclosed that germicidal agents were incorporated into contact lenses. U.S. Pat. No. 4,472,327 discloses that antimicrobial agents may be added to the monomer before polymerization and locked into the polymeric structure of the lens. U.S. Pat. Nos. 5,358,688 and 5,536,861 disclose that contact lenses having antimicrobial properties may be made from quaternary ammonium group containing organosilicone polymers. European patent application EP0604369 discloses that deposit-resistant contact lenses can be prepared from hydrophilic copolymers that are based on 2-hydroxyethyl methacrylate and comonomers containing a quaternary ammonium moiety. Another example is an ocular lens material, disclosed in European patent application EP0947856A2, which comprises a quaternary phosphonium group-containing polymer. A further example is U.S. Pat. No. 5,515,117 which discloses contact lenses and contact lens cases made from materials which comprise polymeric materials and effective antimicrobial components. A still further example is U.S. Pat. No. 5,213,801 which discloses contact lenses made from materials comprising a hydrogel and an antimicrobial ceramic containing at least one metal selected from Ag, Cu and Zn.

The other approach for making antimicrobial medical devices is to form antimicrobial coatings, containing leachable or covalently attached antimicrobial agents, on medical devices. Antimicrobial coatings containing leachable antimicrobial agents may not be able to provide antimicrobial activity over the period of time when used in the area of the human body. In contrast, antimicrobial coating containing covalently bound antimicrobial agents can provide antimicrobial activity over a relatively longer period of time. However, antimicrobial compounds in such coatings may exhibit diminished activity when comparing the activity of the unbound corresponding antimicrobial compounds in solution, unless assisted by hydrolytic breakdown of either the bound antimicrobial compounds or the coating itself. Like the above-described approach, the antimicrobial coating may not be able to provide desired surface properties such as hydrophilicity and/or lubricity and also may have adverse effects on the desired bulk properties of a medical device (for example, the oxygen permeability of a contact lens).

Currently, a wide variety of antimicrobial agents have been proposed to be used as coatings for contact lenses (see, for example, U.S. Pat. No. 5,328,954). Prior known antimicrobial coatings include antibiotics, lactoferrin, metal chelating agents, substituted and unsubstituted polyhydric phenols, amino phenols, alcohols, acid and amine derivatives, and quaternary ammonium group-containing compounds. However, such antimicrobial coatings have disadvantages and are unsatisfactory. The overuse of antibiotics can lead to proliferation of antibiotic-resistant microorganisms. Other coatings may not have broad spectrum antimicrobial activity, may produce ocular toxicity or allergic reactions, or may adversely affect lens properties required for ensuring corneal health and for providing the patient with good vision and comfort.

In spite of the forgoing efforts, there is no commercially viable contact lenses, especially extended-wear contact lenses, which exhibit antimicrobial activities over a long period of time. Therefore, there is still a need for the development of new contact lenses which have high bactericidal efficacy, a broad spectrum of antimicrobial activities, and minimal adverse effects on the wearer's ocular health and comfort. There is also a need for contact lenses which have high bactericidal efficacy, a broad spectrum of antimicrobial activities, and minimal adverse effects on the wearer's ocular health and comfort over a relatively long period of wearing time. Such contact lenses may have increased safety as extended-wear contact lenses which could provide comfort, convenience, and safety.

One object of the invention is to provide a method for making an antimicrobial ophthalmic device which has a relatively high antimicrobial activity over a long period of time when being used, coupled with high oxygen permeability and ion permeability.

Another object of the invention is to provide a cost-effective and efficient process for making an antimicrobial ophthalmic device which has a relatively high antimicrobial activity over a long period of time when being used, coupled with high oxygen permeability and ion permeability.

A further object of the invention is to provide a cost-effective and efficient process for forming an antimicrobial coating on a medical device an antimicrobial ophthalmic device which has a relatively high antimicrobial activity over a long period of time when being used, a high oxygen permeability and a high ion permeability.

SUMMARY OF THE INVENTION

These and other objects of the invention are met by the various aspects of the invention described herein.

The invention, in one aspect, provides a method for making an antimicrobial medical device, preferably an antimicrobial ophthalmic device, more preferably an antimicrobial contact lens, even more preferably an antimicrobial extended wear lens. The method comprises the steps of: obtaining a polymerizable fluid composition comprising a siloxane-containing macromer and a vinylic monomer capable of reducing silver cations; forming a polymerizable dispersion comprising silver nanoparticles and having a stability of at least about 60 minutes, wherein the silver nanoparticles are obtained by adding a desired amount of a soluble silver salt into the fluid composition; introducing an amount of the polymerizable dispersion in a mold for making a medical device; and polymerizing the polymerizable dispersion in the mold to form the antimicrobial medical device containing silver nanoparticles.

The invention, in another aspect, provides a method for making an antimicrobial medical device, preferably an antimicrobial ophthalmic device, more preferably an antimicrobial contact lens, even more preferably an antimicrobial extended wear lens. The method comprises the steps of: obtaining a polymerizable fluid composition comprising a siloxane-containing macromer and a soluble silver salt; forming a polymerizable dispersion comprising silver nanoparticles and having a stability of at least about 60 minutes, wherein the silver nanoparticles are obtained by adding into the fluid composition at least one biocompatible reducing agent; introducing an amount of the polymerizable dispersion in a mold for making a medical device; and polymerizing the polymerizable dispersion in the mold to form the antimicrobial medical device containing silver nanoparticles.

The invention, in still another aspect, provides a method for making an antimicrobial medical device, preferably an antimicrobial ophthalmic device, more preferably an antimicrobial contact lens, even more preferably an antimicrobial extended wear lens. The method comprises the steps of: obtaining a stabilized-silver nano-particle solution or lyophilized stabilized-silver nano-particles; directly dispersing a desired amount of the stabilized-silver nano-particle solution or the lyophilized stabilized-silver nano-particles in a polymerizable fluid composition comprising a siloxane-containing macromer to form a polymerizable dispersion having a stability of at least about 60 minutes; introducing an amount of the polymerizable dispersion in a mold for making a medical device; and polymerizing the polymerizable dispersion in the mold to form the antimicrobial medical device containing silver nanoparticles.

The invention, in a further aspect, provides an antimicrobial medical device, preferably an antimicrobial ophthalmic device, more preferably an antimicrobial contact lens, even more preferably an antimicrobial extended-wear contact lens. The antimicrobial medical device of the invention comprises a polymer matrix and silver nano-particles distributed therein in a substantially uniform manner, wherein the polymer matrix includes a polysiloxane unit, has a high oxygen permeability characterized by a $D_k$ greater than 60 barrers and a high ion permeability characterized by an ionoflux diffusion coefficient of great than $6.0 \times 10^{-4}$ mm$^2$/min, and comprises a water content of at least 15 weight percent when fully hydrated, and wherein the antimicrobial medical device exhibit at least a 5-fold reduction ($\geq 80\%$ inhibition), preferably at least a 1-log reduction ($\geq 90\%$ inhibition), more preferably at least a 2-log reduction ($\geq 99\%$ inhibition), of viable microorganisms.

The invention, in a still further aspect, provide an antimicrobial extended wear contact lens. The antimicrobial extended wear contact lens of the invention comprises a polymer matrix and silver nano-particles distributed therein in a substantially uniform manner, wherein the polymer matrix includes a polysiloxane unit, has a high oxygen permeability characterized by a $D_k$ greater than 60 barrers and a high ion permeability characterized by an ionoflux diffusion coefficient of great than $6.0 \times 10^{-4}$ mm$^2$/min, and comprises a water content of at least 15 weight percent when fully hydrated, and wherein the antimicrobial medical device exhibit at least a 5-fold reduction ($\geq 80\%$ inhibition), preferably at least a 1-log reduction ($\geq 90\%$ inhibition), more preferably at least a 2-log reduction ($\geq 99\%$ inhibition), of viable microorganisms, over a period of at least 7 days, preferably at least 14 days, even more preferably at least 30 days.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

A "medical device", as used herein, refers to a device or a part thereof having one or more surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifices, dental moldings; (6) ophthalmic devices; and (7) cases or containers for storing ophthalmic devices or ophthalmic solutions.

An "ophthalmic device", as used herein, refers to a contact lens (hard or soft), an intraocular lens, a corneal onlay, other ophthalmic devices (e.g., stents, glaucoma shunt, or the like) used on or about the eye or ocular vicinity, "Biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

The term "fluid" as used herein indicates that a material is capable of flowing like a liquid.

A "monomer" means a low molecular weight compound that can be polymerized actinically or thermally or chemically. Low molecular weight typically means average molecular weights less than 700 Daltons.

As used herein, "actinically" in reference to curing or polymerizing of a polymerizable composition or material or a lens-forming material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art. Lens-forming materials are well known to a person skilled in the art.

A "vinylic monomer", as used herein, refers to a low molecular weight compound that has an ethylenically unsaturated group and can be polymerized actinically or thermally. Low molecular weight typically means average molecular weights less than 700 Daltons.

The term "olefinically unsaturated group" is employed herein in a broad sense and is intended to encompass any groups containing at least one >C=C< group. Exemplary ethylenically unsaturated groups include without limitation acryloyl, methacryloyl, allyl, vinyl, styrenyl, or other C=C containing groups.

A "hydrophilic vinylic monomer", as used herein, refers to a vinylic monomer which is capable of forming a homopolymer that can absorb at least 10 percent by weight water when fully hydrated.

A "hydrophobic vinylic monomer", as used herein, refers to a vinylic monomer which is capable of forming a homopolymer that can absorb less than 10 percent by weight water.

A "macromer" refers to a medium to high molecular weight compound or polymer that contains functional groups capable of undergoing further polymerizing/crosslinking reactions. Medium and high molecular weight typically means average molecular weights greater than 700 Daltons. Preferably, a macromer contains ethylenically unsaturated groups and can be polymerized actinically or thermally.

"Molecular weight" of a polymeric material (including monomeric or macromeric materials), as used herein, refers to the number-average molecular weight unless otherwise specifically noted or unless testing conditions indicate otherwise.

A "polymer" means a material formed by polymerizing/crosslinking one or more monomers, macromers and or oligomers.

A "prepolymer" refers to a starting polymer which can be cured (e.g., crosslinked and/or polymerized) actinically or thermally or chemically to obtain a crosslinked and/or polymerized polymer having a molecular weight much higher than the starting polymer. A "crosslinkable prepolymer" refers to a starting polymer which can be crosslinked upon actinic radiation to obtain a crosslinked polymer having a molecular weight much higher than the starting polymer.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to an article, preferably a medical device, and is obtained through a layer-by-layer ("LbL") deposition of polyionic (or charged) and/or non-charged materials on an article. An LbL coating can be composed of one or more layers, preferably one or more bilayers.

The term "bilayer" is employed herein in a broad sense and is intended to encompass: a coating structure formed on a medical device by alternatively applying, in no particular order, one layer of a first polyionic material (or charged material) and subsequently one layer of a second polyionic material (or charged material) having charges opposite of the charges of the first polyionic material (or the charged material); or a coating structure formed on a medical device by alternatively applying, in no particular order, one layer of a first charged polymeric material and one layer of a non-charged polymeric material or a second charged polymeric material. It should be understood that the layers of the first and second coating materials (described above) may be intertwined with each other in the bilayer.

Formation of an LbL coating on a medical device, in particular, an ophthalmic device, may be accomplished in a number of ways, for example, as described in commonly-owned U.S. Pat. Ser. No. 6,451,871 (herein incorporated by reference in its entirety) and commonly-owned pending U.S. patent applications (application Ser. Nos. 09/774942, 09/775104, 10/654,566), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

A medical device having a core material and an LbL coating, which comprises at least one layer of a charged polymeric material and one layer of a non-charged polymeric material that can be non-covalently bonded to the charged polymeric material, can be prepared according to a method disclosed in a co-pending U.S. application, U.S. Ser. No. 10/654,566, entitled "LbL-COATED MEDICAL DEVICE AND METHOD FOR MAKING THE SAME", filed on Sep. 11, 2002, herein incorporated by reference in its entirety.

A "polyquat", as used herein, refers to a polymeric quaternary ammonium group-Containing compound.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

An "antimicrobial medical device", as used herein, refers to a medical device that exhibit at least a 5-fold reduction ($\geqq$80% inhibition), preferably at least a 1-log reduction ($\geqq$90% inhibition), more preferably at least a 2-log reduction ($\geqq$99% inhibition), of viable microorganisms.

An "antimicrobial agent", as used herein, refers to a chemical that is capable of decreasing or eliminating or inhibiting the growth of microorganisms such as that term is known in the art.

"Antimicrobial metals" are metals whose ions have an antimicrobial effect and which are biocompatible. Preferred antimicrobial metals include Ag, Au, Pt, Pd, Ir, Sn, Cu, Sb, Bi and Zn, with Ag being most preferred.

"Silver nanoparticles" refer to particles which is made essentially of silver (Ag) and have a size of less than 1 micrometer. Silver nanoparticles contain silver in $Ag^0$ oxidation state and optionally in $Ag^{1+}$ and/or $Ag^{2+}$ oxidation states. The formation of silver nano-particles in a solution or lens-forming formulation can be confirmed by UV spectroscopy with an absorption peak located in a wavelength range from about 390 nm to about 450 nm, a characteristic of silver nano-particles.

"Antimicrobial metal-containing nanoparticles" refer to particles having a size of less than 1 micrometer and containing at least one antimicrobial metal present in one or more of its oxidation states.

"Antimicrobial metal nanoparticles" refer to particles which is made essentially of an antimicrobial metal and have a size of less than 1 micrometer. The antimicrobial metal in the antimicrobial metal nanoparticles can be present in one or more of its oxidation states.

"Stabilized antimicrobial metal nanoparticles" refer to antimicrobial metal nanoparticles (e.g., silver nanoparticles) which are stabilized by a stabilizer during their preparation or in an LbL coating procedure after their preparation. Stabilized antimicrobial metal nano-particles can be either positively charged or negatively charged or neutral, largely depending on a material (or so-called stabilizer) which is present in a solution for preparing the nano-particles or for coating the nano-particles in a layer-by-layer (LbL) coating process and can stabilize the resultant nano-particles. A stabilizer can be any known suitable material. Exemplary stabilizers include, without limitation, positively charged polyionic materials, negatively charged polyionic materials, polymers, surfactants, acrylic acid, salicylic acid, alcohols and the like.

Formation of an LbL coating on nano-particles may be accomplished by contacting dry or wet nano-particles with one or more coating solution of a stabilizer, for example, as described in commonly-owned U.S. Pat. Ser. No. 6,451,871 (herein incorporated by reference in its entirety) and commonly-owned pending U.S. patent applications (application Ser. Nos. 09/774942, 09/775104, 10/654,566, 60/530,959), herein incorporated by reference in their entireties. For example, nano-particles can be stabilized in a coating process, which comprises (1) applying a coating of one or more polyionic materials onto the surfaces of nano-particles by contacting the nano-particles with a solution of the one or more polyionic materials; filtering the solution with nano-particles, optionally washing the filtered nano-particles; and optionally drying the filtered nano-particles coated with the one or more polyionic materials.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Dye" means a substance that is soluble in a solvent and that is used to impart color. Dyes are typically translucent and absorb but do not scatter light. Any suitable biocompatible dye can be used in the present invention.

A "Pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3 \text{ oxygen})/(cm^2)(sec)(mm^2 \text{ Hg})] \times 10^{-9}$$

The intrinsic "oxygen permeability", Dk, of a lens material does not depend on lens thickness. Intrinsic oxygen permeability is the rate at which oxygen will pass through a material. Oxygen permeability is conventionally expressed in units of barrers, where "barrer" is defined as:

$$[(cm^3 \text{ oxygen})(mm)/(cm^2)(sec)(mm^2 \text{ Hg})] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm).

The cornea receives oxygen primarily from the corneal surface which is exposed to the environment, in contrast to other tissues which receives oxygen from blood flow. Thus, an ophthalmic lens which may be worn on the eye for extended periods of time must allow sufficient oxygen to permeate through the lens to the cornea to sustain corneal health. One result of the cornea receiving an inadequate amount of oxygen is that the cornea will swell. Therefore, the oxygen transmissibility of an extended-wear lens from the outer surface to the inner surface must be sufficient to prevent any substantial corneal swelling during the period of extended wear. It is known that the cornea swells approximately 3% to 4% during overnight periods of sleep when the eyelids are closed, as a result of oxygen deprivation. It is also known that wearing a typical contact lens, such as ACUVUE (Johnson & Johnson), for a period of about 8 hours (overnight wear) causes corneal swelling of about 11%. However, a preferred extended-wear contact lens will produce, after wear of about 24 hours, including normal sleep periods, corneal swelling of less than about 8%, more preferably less than about 6%, and most preferably less than about 4%. A preferred extended-wear contact lens will produce, after wear of about 7 days, including normal sleep periods, corneal swelling of less than about 10%, more preferably less than about 7%, and most preferably less than about 5%.

The oxygen permeability of a lens and oxygen transmissibility of a lens material may be determined by the method disclosed by Nicolson et al. (U.S. Pat. No. 5,760,100), herein incorporated by reference in its entirety. In accordance with the invention, a high oxygen permeability in reference to a material or an ophthalmic device characterized by having an apparent (directly measured) oxygen permeability of at least 60 barrers or larger measured (preferably with a sample (film or lens) of 100 microns in thickness) according to a coulometric method described in Examples.

The "ion permeability" through a lens correlates with both the Ionoflux Diffusion Coefficient and the Ionoton Ion Permeability Coefficient.

The Ionoflux Diffusion Coefficient, D, is determined by applying Fick's law as follows:

$$D = -n'/(A \times dc/dx)$$

where n'=rate of ion transport [mol/min]
A=area of lens exposed [mm$^2$]
D=Ionoflux Diffusion Coefficient [mm$^2$/min]
dc=concentration difference [mol/L]
dx=thickness of lens [mm]

The Ionoton Ion Permeability Coefficient, P, is then determined in accordance with the following equation:

$$\ln(1-2C(t)/C(0)) = -2APt/Vd$$

where: C(t)=concentration of sodium ions at time t in the receiving cell
C(0)=initial concentration of sodium ions in donor cell
A=membrane area, i.e., lens area exposed to cells
V=volume of cell compartment (3.0 ml)
d=average lens thickness in the area exposed
P=permeability coefficient An Ionoflux Diffusion Coefficient, D, of greater than about $0.2 \times 10^{-3}$ mm$^2$/min is preferred, while greater than about $0.64 \times 10^{-3}$ mm$^2$/min is more preferred and greater than about $1.0 \times 10^{-3}$ mm$^2$/min is most preferred.

It is known that on-eye movement of the lens is required to ensure good tear exchange, and ultimately, to ensure good corneal health. Ion permeability is one of the predictors of on-eye movement, because the permeability of ions is believed to be directly proportional to the permeability of water.

It has been theorized by Nicolson et al. (U.S. Pat. No. 5,760,100), herein incorporated by reference in its entirety, that water permeability is an exceptionally important feature for an extended-wear lens which includes oxyperm polymers such as those disclosed herein. Siloxane-containing materials having high oxygen permeability and low water permeability tend to adhere strongly to the eye, thereby stopping on-eye movement. The ability to pass water through the lens is believed to allow a siloxane-containing polymeric lens to move on the eye, where the movement occurs via forces exerted by water being sqeezed out of the lens. The water permeability of the lens is also believed important in replenishing lens water content once pressure is removed.

Nicolson et al. (U.S. Pat. No. 5,760,100) also found that above a certain threshhold of ion permeability through a lens, from the inner surface of the lens to the outer, or vice versa, the lens will move on the eye, and below the threshold the lens will adhere to the eye. The ion permeability through a lens correlates with both the Ionoflux Diffusion Coefficient and the Ionoton Ion Permeability Coefficient.

The water permeability of a lens may be determined by the Hydrodell Technique described by Nicolson et al. in U.S. Pat. No. 5,849,811. This technique may be used to determine the likelihood of adequate on-eye movement.

The ophthalmic lenses of one embodiment of the present invention have a Hydrodell Water Permeability Coefficient of greater than about $0.2 \times 10^{-6}$ cm$^2$/min. The ophthalmic lenses in a preferred embodiment of the invention have Hydrodell Water Permeability Coefficient of greater than about $0.3 \times 10^{-6}$ cm$^2$/min. The ophthalmic lenses in a preferred embodiment of the invention have Hydrodell Water Permeability Coefficient of greater than about $0.4 \times 10^{-6}$ cm$^2$/min.

The water content of a lens can be measured according to Bulk Technique as disclosed in U.S. Pat. No. 5,760,100, herein incorporated by reference in its entirety. Preferably, the lens has a water content of at least 20 weight percent when fully hydrated, based on the total lens weight.

The present invention is generally directed to methods for making an antimicrobial medical device having silver nano-particles distributed uniformly therein and to an antimicrobial medical device made therefrom. The present invention is partly based on the discovery that silver nano-particles distributed in a medical device can impart to the medical device an effective antimicrobial capability over a long period of time. It is believed that silver nano-particles can release, at an extremely slow rate, silver ions which in turn can leach slowly out of a medical device and therefore decrease or eliminate or inhibit the growth of microorganisms. The present invention is also partly based on the discovery that uniform incorporation of silver nano-particles in a contact lens has a negligible adverse impact on the optical properties of the contact lens. The present invention further is partly based on the discovery that an antimicrobial medical device, which has silver nano-particles incorporated and distributed uniformly in the polymer matrix of the ophthalmic device to impart antimicrobial capability without significantly adverse effects on the desired bulk properties of the ophthalmic device, such as oxygen permeability, ion or water permeability, can be produced according to one of cost-effective and efficient processes developed herein.

By using a process of the invention, one can prepare, in an easy and non-intrusive manner, a polymerizable dispersion containing silver nano-particles and having a stability of at least about 60 minutes, preferably at least about 4 hours, more preferably at least about 8 hours, even more preferably at least about 15 hours. As used herein, the term "stability" in reference to a dispersion means a period of time over which no observable agglomeration and/or precipitation occurs in the dispersion. The term "non-intrusive" in reference to a polymerizable dispersion preparation means that during its preparation minimal or no undesirable partial polymerization occurs in the prepared polymerizable dispersion. Typically, vigorously stirring and/or sonication is used to disperse particles in a solution to form a dispersion. However, when preparing a polymerizable dispersion for making an ophthalmic device, such vigorously stirring and sonication, especially sonication for relatively extended period of time, should be avoided to minimize or eliminate partial polymerization.

There are several unique advantages associated with a method of the invention.

First, according to a method of the invention, a polymerizable dispersion containing siliver nano-particles can be easily prepared from any lens formulation for making any contact lenses with minimal modification of preparing procedure. Exemplary lens formulations include without limitation the formulation of nelfilcon, lotrafilcon A, lotrafilcon B, etafilcon A, genfilcon A, lenefilcon A, polymacon, acquafilcon A, balafilcon, and the like.

Second, one can prepare a silver nanoparticle-containing polymerizable dispersion having any desired concentration of silver nano-particles.

Third, because of its high stability, a silver nanoparticle-containing polymerizable dispersion can be prepared in well advance before production of contact lenses. Therefore, one can have flexibility in production scheduling of lens productions.

Fourth, because of its high stability, silver nano-particles can be uniformly distributed in a contact lens. Unstable polymerizable dispersion containing silver nanoparticles may not be suitable for production of antimicrobial contact lenses comprising siver nano-particles uniformly distributed therein.

By using a process of the invention, a prepared antimicrobial medical device can have at least one of bulk properties selected from the group consisting of: a high oxygen permeability characterized by a $D_k$ greater than 60 barrers; a high ion permeability characterized by an ionoflux diffusion coefficient of great than $6.0 \times 10^{-4}$ mm$^2$/min; a water content of at least 15 weight percent when fully hydrated; an antimicrobial acitivity characterized by having at least a 5-fold reduction ($\geqq$80% inhibition), preferably at least a 1-log reduction ($\geqq$90% inhibition), more preferably at least a 2-log reduction ($\geqq$99% inhibition), of viable microorganisms (e.g., *Pseudomonas aeruginosa* GSU #3, or *Staphylococcus aureus* ATCC #6538); a prolong antimicrobial activity (i.e., effective antimicrobial activity after direct contact with a body fluid over an extended period of time).

As used herein, a "prolong antimicrobial activity" is characterized by having at least a 5-fold reduction ($\geqq$80% inhibition), preferably at least a 1-log reduction ($\geqq$90% inhibition), more preferably at least a 2-log reduction ($\geqq$99% inhibition), of viable microorganisms (e.g., *Pseudomonas aeruginosa* GSU #3, or *Staphylococcus aureus* ATCC #6538) after at least 5, preferably at least 10, more preferably at least 20, even more preferably at least 30 consecutive soaking/rinsing cycles, each cycle comprising soaking/rinsing one lens in a phosphate buffered saline (PBS) for a period of time from about 24 to about 72 hours, as shown in Example.

The invention, in one aspect, provides a method for making an antimicrobial medical device, preferably an antimicrobial ophthalmic device, more preferably an antimicrobial contact lens, even more preferably an antimicrobial extended wear lens. The method comprises the steps of: obtaining a polymerizable fluid composition comprising a siloxane-containing macromer and a vinylic monomer capable of reducing silver cations; forming a polymerizable dispersion comprising silver nanoparticles and having a stability of at least about 60 minutes, preferably at least about 4 hours, more preferably at least about 8 hours, even more preferably at least about 15 hours, wherein the silver nanoparticles are obtained by adding a desired amount of a soluble silver salt into the fluid composition; introducing an amount of the polymerizable dispersion in a mold for making a medical device; and polymerizing the polymerizable dispersion in the mold to form the antimicrobial medical device containing silver nanoparticles.

In a preferred embodiment, the resultant antimicrobial medical device comprises at least 10 ppm, preferably at least 25 ppm, more preferably at least 40 ppm, even more preferably at least 60 ppm silver nanoparticles.

In accordance with the present invention, a polymerizable fluid composition can be a solution or a solvent-free liquid or melt at a temperature below 60° C.

In accordance with the present invention, a polymerizable fluid composition can be any formulations for making soft contact lenses. Exemplary formulations include without limitation the formulation of lotrafilcon A, lotrafilcon B, etafilcon A, genfilcon A, lenefilcon A, polymacon, acquafilcon A, and balafilcon.

Where a polymerizable fluid composition is a solution, it can be prepared by dissolving at least one siloxane-containing macromer and all other desired components in any suitable solvent known to a person skilled in the art. Examples of suitable solvents are water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

In accordance with the present invention, any know suitable siloxane-containing macromer can be used to prepare a polymerizable fluid composition.

Preferably, the polymerizable fluid composition comprises a siloxane-containing macromer selected from the group consisting of Macromer A, Macromer B, Macromer C, and Macromer D.

Macromer A

Macromer A is a polysiloxane macromer having the segment of the formula:

CP—PAO-DU-ALK—PDMS-ALK-DU-PAO—CP where PDMS is a divalent poly(disubstituted siloxane), ALK is an alkylene or alkylenoxy group having at least 3 carbon atoms, DU is a diurethane-containing group, PAO is a divalent polyoxyalkylene, and CP is selected from acrylates and methacrylates, wherein said macromer has a number-average molecular weight of 2000 to 10,000.

A preferred polysiloxane macromer segment is defined by the formula

CP—PAO-DU-ALK—PDMS-ALK-DU-PAO—CP where PDMS is a divalent poly(disubstituted siloxane); CP is an isocyanatoalkyl acrylate or methacylate, preferably isocyanatoethyl methacrylate, where the urethane group is bonded to the terminal carbon on the PAO group; PAO is a divalent polyoxyalkylene (which may be substituted), and is preferably a polyethylene oxide, i.e., (—CH$_2$CH$_2$—O—)$_m$CH$_2$CH$_2$— where m may range from about 3 to about 44, more preferably about 4 to about 24; DU is a diurethane, preferably including a cyclic structure, where an oxygen of the urethane linkage (1) is bonded to the PAO group and an oxygen of the urethane linkage (2) is bonded to the ALK group; and ALK is an alkylene or alkylenoxy group having at least 3 carbon atoms, preferably a branched alkylene group or an alkylenoxy group having 3 to 6 carbon atoms, and most preferably a sec-butyl (i.e., —CH$_2$CH$_2$CH(CH$_3$)—) group or an ethoxypropoxy group (e.g., —O—(CH$_2$)$_2$—O—(CH$_2$)$_3$—).

It will be noted that the DU group can be formed from a wide variety of diisocyanates or triisocyanates, including aliphatic, cycloaliphatic or aromatic polyisocyanates. These isocyanates include, without limitation thereto, ethylene diisocyanate; 1,2-diisocyanatopropane; 1,3-diisocyanatopropane; 1,6-diisocyanatohexane; 1,2-diisocyanatocyclohexane; 1,3-diisocyanatocyclohexane; 1,4-diisocyanatobenzene, bis(4-isocyanatocyclohexyl)methane; bis(4-isocyanatocyclohexyl)methane; bis(4-isocyanatophenyl)methane; 1,2- and 1,4-toluene diisocyanate; 3,3-dichloro-4,4'-diisocyanatobiphenyl; tris(4-isocyanatophenyl)methane; 1,5-diisocyanatonaphthalene; hydrogenated toluene diisocyanate; 1-isocyanatomethyl-5-isocyanato-1,3,3-trimethylcyclohexane (i.e., isophorone diisocyanate); 1,3,5-tris(6-isocyanatohexyl)

biuret; 1,6-diisocyanato-2,2,4-(2,4,4)-trimethylhexane; 2,2'-diisocyanatodiethyl fumarate; 1,5-diisocyanato-1-carboxypentane; 1,2-, 1,3-, 1,6-, 1,7-, 1,8-, 2,7- and 2,3-diisocyanatonaphthalene; 2,4- and 2,7-diisocyanato-1-methylnaphthalene; 1,4-diisocyanatomethylcyclohexane; 1,3-diisocyanato-6(7)-methylnaphthalene; 4,4'-diisocyanatobiphenyl; 4,4'-diisocyanato-3,3'-dimethoxybisphenyl; 3,3'- and 4,4'-diisocyanato-2,2'-dimethylbisphenyl; bis(4-isocyanatophenyl)ethane; bis(4-isocyanatophenyl ether); 1,2- or 1,4-toluene diisocyanate; and mixtures thereof. Preferably DU is formed from isophorone diisocyanate or toluene diisocyanate, and more preferably, isophorone diisocyanate, where one isomeric diurethane structure of isophorone diisocyanate is defined above.

A preferred polysiloxane macromer segment has the following formula:

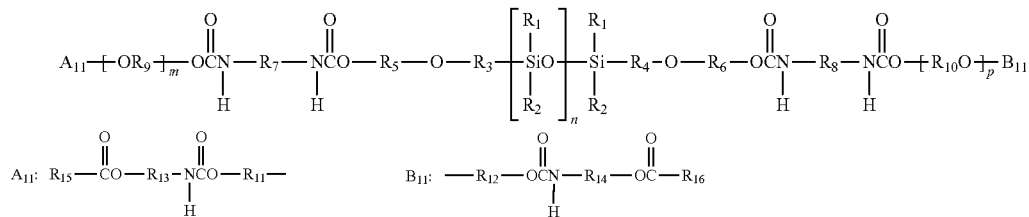

wherein: $R_1$ and $R_2$ are selected from $C_1$-$C_6$ alkyl; $R_3$, $R_4$, $R_5$, and $R_6$ are selected from $C_1$-$C_6$ alkylene; $R_7$ and $R_8$ are selected from linear or branched alkylene and bivalent cycloalkylene; $R_9$, $R_{10}$, $R_{11}$, and $R_{12}$ are selected from $C_1$-$C_2$ alkylene; $R_{13}$ and $R_{14}$ are selected from $C_1$-$C_6$ alkylene; $R_{15}$ and $R_{16}$ are selected from linear or branched lower alkenylene; m and p, independently of one another, are about 3 to about 44; and n is about 13 to about 80, wherein said macromer has a number-average molecular weight of 2000 to 10,000.

The polysiloxane macromer may be synthesized by the following preferred process. At about room temperature (about 20°-25° C.), poly(dimethylsiloxane)dialkanol having hydroxyalkyl (e.g., hydroxy-sec-butyl) or hydroxyalkoxy (e.g., hydroxyethylpropoxy) end groups and having a molecular weight of about 2000 to 3000 preferably about 2200, i.e., having about 28 repeating siloxane groups) is reacted with isophorone diisocyanate at about a 1:2 molar ratio, using about 0.2 weight percent (based on polydimethylsiloxane)dibutyltin dilaurate added as a catalyst The reaction is carried out for about 36 to 60 hours. To this mixture is added poly(ethylene glycol) having a molecular weight of about 400 to 1200 (more preferably about 500 to 700) at about a 2:1 or 2.1:1 molar ratio with respect to the PDMS, about 0.4 to 0.5 weight percent dibutyltin dilaurate (based on polyethylene glycol weight), and chloroform sufficient to ensure substantial mixture homogeneity. The mixture is agitated for about 12 to 18 hours, then held at a temperature of about 44° to 48° C. for about 6 to 10 hours. Excess chloroform is evaporated therefrom at about room temperature to produce a composition having about 50 weight percent solids. Then, isocyanatoethyl methacrylate is added to the mixture in about a 2:1 to 2.3:1 molar ratio with respect to PDMS. The mixture is agitated at room temperature for about 15 to 20 hours. The resulting solution contains a polysiloxane macromer having the composition described above and a number-average molecular weight of about 2000 to 10,000, more preferably about 3000 to 5000.

Macromer B

Macromer B is a polysiloxane-comprising perfluoroalkyl ether and has the formula:

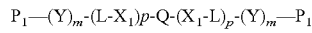

In which each $P_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each $X_1$, independently of the others, is —NHCO—, —CON—, —NHCONH—, —COO—, —OCO—, —NHCOO— or —OCONH—; and Q is a bivalent polymer fragment consisting of the segments:

(a) -(E)$_k$-Z—CF$_2$—(OCF$_2$)$_x$—(OCF$_2$CF$_2$)$_y$—OCF$_2$—Z-(E)$_k$-, where x+y is a number in the range of from 10 to 30;

each Z, independently of the others, is a divalent radical having up to 12 carbon atoms or Z is a bond;

each E, independently of the others, is —(OCH$_2$CH$_2$)$_q$—, where q has a value of from 0 to 2, and where the link -Z-E- represents the sequence -Z—(OCH$_2$CH$_2$)$_q$—; and k is 0 or 1;

(b)

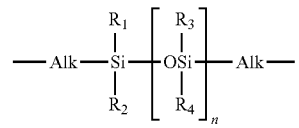

where n is an integer from 5 to 100; Alk is alkylene having up to 20 carbon atoms; 80-100% of the radicals $R_1$, $R_2$, $R_3$ and $R_4$, independently of one another, are alkyl and 0-20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NHCOO— or OCONH—;

with the provisos that there must be at least one of each segment (a), (b), and (c) in Q, that each segment (a) or (b) has a segment (c) attached to it, and that each segment (c) has a segment (a) or (b) attached to it.

The number of segments (b) in the polymer fragment Q is preferably greater than or equal to the number of segments (a). The ratio between the number of segments (a) and (b) in the polymer fragment Q is preferably 3:4, 2:3, 1:2 or 1:1. The molar ratio between the number of segments (a) and (b) in the polymer fragment Q is more preferably 2:3, 1:2 or 1:1.

The mean molecular weight of the polymer fragment Q is in the range of about 1000 to about 20000, preferably in the range of about 3000 to about 15000, particularly preferably in the range of about 5000 to about 12000.

The total number of segments (a) and (b) in the polymer fragment Q is preferably in the range of 2 to about 11, particularly preferably in the range of 2 to about 9, and in particular in the range of 2 to about 7. The smallest polymer unit Q is preferably composed of one perfluoro segment (a), one siloxane segment (b) and one segment (c).

In a preferred embodiment of the polymer fragment Q, which preferably has a composition in the above-mentioned ratios, the polymer fragment Q is terminated at each end by a siloxane segment (b).

The compositions in a bivalent polymer fragment Q always correspond above and below to a mean statistical composition. This means that, for example, even individual block copolymer radicals containing identical recurring units are included, so long as the final mean statistical composition is as specified.

$X_1$ is preferably —NHCONH—, —NHCOO— or —OCONH—, particularly preferably —NHCOO— or —OCONH—.

The $X_2$—R—$X_2$ segment is preferably a radical derived from a diisocyanate, where each $X_2$, independently of the other, is NHCONH—, —NHCOO— or —OCONH—, in particular —NHCOO— or —OCONH—.

Z is preferably a bond, lower alkylene or —CONH-arylene, in which the —CO-moiety is linked to a $CF_2$ group. Z is particularly preferably lower alkylene, in particular methylene.

q is preferably 0, 1, 1.5 or 2, particularly preferably 0 or 1.5.

The perfluoroalkoxy units $OCF_2$ and $OCF_2CF_2$ with the indices x and y in segment (a) can either have a random distribution or be in the form of blocks in a chain. The sum of the indices x+y is preferably a number in the range of 10 to 25, particularly preferably of 10 to 15. The ratio x:y is preferably in the range of 0.5 to 1.5, in particular in the range of 0.7 to 1.1.

A free-radical-polymerizable group $P_1$ is, for example, alkenyl alkenylaryl or alkenylarylenealkyl having up to 20 carbon atoms. Examples of alkenyl are vinyl, allyl, 1-propen-2-yl, 1-buten-2-, -3- and 4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, NHCO— or —CONH—, particularly preferably —COO—, —OCO—, NHCO— or —CONH—, and in particular, —COO— or —OCO—.

In a preferred embodiment, the indices, m and p, are not simultaneously zero. If p is zero, m is preferably 1.

L is preferably alkylene, arylene, a saturated bivalent cycloaliphatic group having 6 to 20 carbon atoms, arylenealkylene, alkylenearylene, alkylenearylenealkylene or arylenealkylenearylene.

Preferably, L is a divalent radical having up to 12 carbon atoms, particularly preferably a divalent radical having up to 8 carbon atoms. In a preferred embodiment, L is furthermore alkylene or arylene having up to 12 carbon atoms. A particularly preferred embodiment of L is lower alkylene, in particular lower alkylene having up to 4 carbon atoms.

The divalent radical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred embodiment, R is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, R is alkylene or arylene having up to 12 carbon atoms or a saturated bivalent cycloaliphatic group having 6 to 14 carbon atoms.

In a preferred embodiment, R is alkylene or arylene having up to 10 carbon atoms or a saturated bivalent cycloaliphatic group having 6 to 10 carbon atoms.

In a particularly preferred meaning, R is a radical derived from a diisocyanate, for example from hexane 1,6diisocyanate, 2,2,4-trimethylhexane 1,6-diisocyanate, tetramethylene diisocyanate, phenylene 1,4diisocyanate, toluene 2,4-diisocyanate, toluene 2,6diisocyanate, m- or p-tetramethylxylene diisocyanate, isophorone diisocyanate or cyclohexane 1,4-diisocyanate.

In a preferred meaning, n is an integer from 5 to 70, particularly preferably 10 to 50, in particular 14 to 28.

In a preferred meaning, 80-100%, preferably 85-100%, in particular 90-100%, of the radicals $R_1$, $R_2$, $R_3$ and $R_4$ are, independently of one another, lower alkyl having up to 8 carbon atoms, particularly preferably lower alkyl having up to 4carbon atoms, especially lower alkyl having up to 2 carbon atoms. A further particularly preferred embodiment of $R_1$, $R_2$, $R_3$ and $R_4$ is methyl.

In a preferred meaning, 0-20%, preferably 0-15%, in particular 0-10%, of the radicals $R_1$, $R_2$, $R_3$ and $R_4$ are, independently of one another, lower alkenyl, unsubstituted or lower alkyl- or lower alkoxy-substituted phenyl or cyano(lower alkyl).

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene, 3-pentylene, and the like.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylenephenylene or phenylenemethylenephenylene.

Macromer B can be prepared by known processes, for example as described in U.S. Pat. No. 5,849,811, herein incorporated by reference.

Macromer C

Macromer C are a class of macromers which contain free hydroxyl groups. This class of macromers are built up, for example, from an amino-alkylated polysiloxane which is derivatized with at least one polyol component containing an unsaturated polymerizable side chain. Polymers can be prepared on the one hand from this class of macromers according to the invention by homopolymerization. The macromers mentioned furthermore can be mixed and polymerized with one or more hydrophilic and/or hydrophobic comonomers. A special property of the macromers according to the invention is that they function as the element which controls microphase separation between selected hydrophilic and hydrophobic components in a crosslinked end product. The hydrophilic/hydrophobic microphase separation is in the region of less than 300 nm. The macromers are preferably crosslinked at the phase boundaries between, for example, an acrylate comonomer on the one hand and an unsaturated polymerizable side chain of polyols bonded to polysiloxane on the other hand, by covalent bonds and additionally by reversible physical interactions, for example hydrogen bridges. These are formed, for example, by numerous amide or urethane groups. The continuous siloxane phase which exists in the phase composite has the effect of producing a surprisingly high permeability to oxygen.

In an embodiment, macromer c comprises at least one segment of the formula (I):

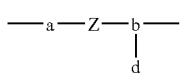
(I)

in which (a) is a polysiloxane segment, (b) is a polyol segment which contains at least 4 C atoms, Z is a segment (c) or a group $X_1$, (c) is defined as $X_2$—R—$X_2$, wherein R is a bivalent radical of an organic compound having up to 20 C atoms and each $X_2$ independently of the other is a bivalent radical which contains at least one carbonyl group, $X_1$ is defined as $X_2$, and (d) is a radical of the formula (II):

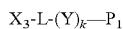
(II)

in which $P_1$ is a group which can be polymerized by free radicals; Y and $X_3$ independently of one another are a bivalent radical which contains at least one carbonyl group; k is 0 or 1; and L is a bond or a divalent radical having up to 20 C atoms of an organic compound.

A polysiloxane segment (a) is derived from a compound of the formula (III):

(III)

in which n is an integer from 5 to 500; 99.8-25% of the radicals $R_1$, $R_2$, $R_3$, $R_4$, $R_5$ and $R_6$ independently of one another are alkyl and 0.2-75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-$NH_2$ or alk-$(OCH_2)$m—$(OCH_2)$p-$OR_7$, $R_7$ is hydrogen or lower alkyl, alk is alkylene, and m and p independently of one another are an integer from 0 to 10, one molecule containing at least one primary amino or hydroxyl group.

The alkylenoxy groups —$(OCH_2CH_2)_m$ and —$(OCH_2)_p$ in the siloxane of the formula (III) are either distributed randomly in a ligand alk-$(OCH_2CH_2)_m$—$(OCH_2)_p$—$OR_7$ or are distributed as blocks in a chain.

A polysiloxane segment (a) is linked a total of 1-50 times, preferably 2-30 times, and in particular 4-10 times, via a group Z with a segment (b) or another segment (a), Z in an a-Z-a sequence always being a segment (c). The linkage site in a segment (a) with a group Z is an amino or hydroxyl group reduced by one hydrogen.

In a preferred embodiment, a polysiloxane segment is derived from a compound of the formula (III) in which the radicals $R_1$, $R_2$, $R_3$, $R_4$, $R_5$ and $R_6$ are a total of 1-50 times, more preferably 2-30 times, and in particular 4-10 times, independently either terminally or pendently aminoalkyl or hydroxyalkyl, the other variables being as defined above.

In a preferred embodiment, a polysiloxane segment is derived from a compound of the formula (III) in which 95-29% of the radicals $R_1$, $R_2$, $R_3$, $R_4$, $R_5$ and $R_6$ independently of one another are alkyl and 5-71% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-$NH_2$ or alk-$(OCH_2CH_2)_m$—$(OCH_2)_p$—$OR_7$, and in which the variables are as defined above.

In a preferred meaning, n is an integer from 5 to 400, more preferably 10 to 250 and particularly preferably 12 to 125.

In a preferred meaning, the two terminal radicals $R_1$ and $R_6$ are aminoalkyl or hydroxyalkyl, the other variables being as defined above.

In another preferred meaning, the radicals $R_4$ and $R_5$ are 1-50 times, more preferably 2-30 times and in particular 4-10 times pendently aminoalkyl or hydroxyalkyl and the other variables are as defined above.

In another preferred meaning, the radicals $R_1$, $R_2$, $R_3$, $R_4$, $R_5$ and $R_6$ are a total of 1-50 times, more preferably 2-30 times and in particular 4-10.times, independently both terminally and pendently aminoalkyl or hydroxyalkyl and the other variables are as defined above.

If Z is $X_1$, $X_1$ is a bivalent group which contains at least one carbonyl group. A carbonyl group mentioned is flanked in any manner, if appropriate, by —O—, —CONH—, —NHCO— or —NH—.

Examples of bivalent groups Z are typically carbonyls, esters, amides, urethanes, ureas or carbonates.

$X_1$ is preferably an ester, amide, urethane or urea group, in particular an ester or amide group.

$X_2$ is defined in the same way as $X_1$ and is preferably an ester, amide, urethane, carbonate or urea group, more preferably an ester, amide, urethane or urea group and in particular an amide, urethane or urea group.

If Z in formula (I) is $X_1$, a polyol segment b is preferably understood as meaning a polyol derived from a carbohydrate, carbohydrate monolactone or carbohydrate dilactone. A carbohydrate is understood as meaning a mono-, di-, tri-, tetra-, oligo- or polysaccharide. A carbohydrate lactone is understood as meaning the lactone of an aldonic or uronic acid. An aldonic or uronic acid is, for example, a carboxylic acid formed by oxidation of a mono-, di-, tri-, tetra-, oligo- or polysaccharide. Examples of aldonic acid lactones are gluconolactone, galactonolactone, lactobionolactone or maltoheptaonolactone; examples of uronic acid lactones are glucuronic acid lactone, mannuronic acid lactone or iduronic acid lactone. An example of a carbohydrate dilactone is D-glucaro-1,4:6,3-dilactone.

A carbohydrate lactone reacts, for example, with a primary amino group or a hydroxyl group of segment (a) to form a covalent amide or ester bond of the type $X_1$. Such linkages are the constituent of a further preferred embodiment of macromers according to the invention. Such macromers have an alternating distribution of segments of type (a) and (b) which are interrupted by $X_1$.

In another embodiment, macromer C is defined by the formula (IV):

in which the variables are as defined above.

In another embodiment, macromer C is defined by the formula (V):

in which the polysiloxane segment (a) contains q pendent ligands; x is 0, 1 or 2; q has an average numerical value of 1-20, preferably 1-10, and in particular 1-5; and the segments (b) in a macromer according to the formula (V) are linked in total (per molecule) with up to 20, preferably with up to 15, and in particular with up to 6 polymerizable segments (d).

In another embodiment, macromer C has the formula (VI):

in which a linear sequence is present; x is 0, 1 or 2; q has an average numerical value of 1-20, preferably 1-10, and in particular 1-5; and the segments (b) in a macromer according to the formula (VI) are linked in total (per molecule) with up to 20, preferably with up to 15, and in particular with up to 6 polymerizable segments (d).

In another embodiment, macromer C has the formula (VII):

in which x is 0, 1 or 2; and the average number of segments (d) per molecule of the formula (VII) is preferably in the range from 2 to 5, and very preferably is in the range from 3 to 4.

A polyol segment (b) is derived from a polyol which carries no lactone group if the group Z is a segment (c). Examples of such polyols are a 1,2-polyol, for example the reduced monosaccharides, for example mannitol, glucitol, sorbitol or iditol, a 1,3-polyol, for example polyvinyl alcohol (PVA), which is derived from partly or completely hydrolysed polyvinyl acetate, and furthermore amino-terminal PVA telomers, aminopolyols, aminocyclodextrins, aminomono-, -di-, -tri-, -oligo- or -polysaccharides or cyclodextrin derivatives, for example hydroxypropylcyclodextrin. An abovementioned carbohydrate dilactone can be reacted, for example, with preferably 2 equivalents of an amino-terminal PVA telomer to give a polyol macromer which carries, in the central part, the carbohydrate compound derived from the dilactone. Such polyols of this composition are likewise understood to be a suitable polyol.

As illustrated in formula (I), a segment (b) carries at least one vinylic polymerizable segment (d), a linkage of a segment (d) via the bivalent radical $X_3$ thereof to an amino or hydroxyl group, of a segment (b), reduced by a hydrogen atom being intended.

A vinylic polymerizable segment (d) is incorporated either terminally or pendently preferably 1-20 times, more preferably 2-15 times, and in particular 2-6 times, per macromer molecule according to the invention.

A vinylic polymerizable segment (d) is incorporated terminally and also pendently as desired (as a terminal/pendent mixture) preferably 1-20 times, more preferably 2-15 times and in particular 2-6 times, per macromer molecule according to the invention.

A group $P_1$ which can be polymerized by free radicals is, for example, alkenyl, alkenylaryl or alkenylarylenealkyl having up to 20 C atoms. Examples of alkenyl are vinyl, allyl, 1-propen-2-yl, 1-buten-2- or -3- or -4-yl, 2-buten-3-yl and the isomers of pentenyl, hexenyl, octenyl, decenyl or undecenyl. Examples of alkenylaryl are vinylphenyl, vinylnaphthyl or allylphenyl. An example of alkenylarylenealkyl is vinylbenzyl.

$P_1$ is preferably alkenyl or alkenylaryl having up to 12 C atoms, more preferably alkenyl having up to 8C atoms and in particular alkenyl having up to 4 C atoms.

L is preferably alkylene, arylene, a saturated bivalent cycloaliphatic group having 6 to 20 carbon atoms, arylenealkylene, alkylenearylene, alkylenearylenealkylene or arylenealkylenearylene. In a preferred meaning, L furthermore is preferably a bond.

In a preferred meaning, L is a divalent radical having up to 12 C atoms, and more preferably a divalent radical having up to 8 C atoms. In a preferred meaning, L furthermore is alkylene or arylene having up to 12 C atoms. A very preferred meaning of L is lower alkylene, in particular lower alkylene having up to 4C atoms.

Y is preferably a carbonyl, ester, amide or urethane group, in particular a carbonyl, ester or amide group, and very preferably a carbonyl group.

In another preferred meaning, Y is absent, i.e., k is 0.

In a preferred meaning, $X_3$ is a urethane, urea, ester, amide or carbonate group, more preferably a urethane, urea, ester or amide group, and in particular a urethane or urea group.

A vinylic polymerizable segment (d) is derived, for example, from acrylic acid, methacrylic acid, methacryloyl chloride, 2-isocyanatoethyl methacrylate (IEM), allyl isocyanate, vinyl isocyanate, the isomeric vinylbenzyl isocyanates or adducts of hydroxyethyl methacrylate (HEMA) and 2,4-tolylene diisocyanate (TDI) or isophorone diisocyanate (IPDI), in particular the 1:1 adduct.

A preferred embodiment of segment (d) is incorporated either terminally or pendently or as a terminal/pendent mixture 5 times.

The diradical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred meaning, R is alkylene, arylene, alkylenearylene, arylenealkylene or arylenealkylenearylene having up to 14 carbon atoms or a saturated bivalent cycloaliphatic group having 6 to 14 carbon atoms.

In a preferred meaning, R is alkylene, arylene, alkylenearylene or arylenealkylene having up to 14 carbon atoms, or a saturated bivalent cycloaliphatic group having 6 to 14 carbon atoms.

In a preferred meaning, R is alkylene or arylene having up to 12 carbon atoms, or a saturated bivalent cycloaliphatic group having 6 to 14 carbon atoms.

In a preferred meaning, R is alkylene or arylene having up to 10 carbon atoms, or is a saturated bivalent cycloaliphatic group having 6 to 10 carbon atoms.

In a very preferred meaning, a segment (c) is derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

A preferred embodiment of segment (c) is furthermore derived from a diisocyanate in which the isocyanate groups have different reactivities. The different reactivity is influenced, in particular, by the spatial requirements and/or electron density in the neighbourhood of an isocyanate group.

The average molecular weight of a macromer according to the invention is preferably in the range from about 300 to about 30,000, very preferably in the range from about 500 to about 20,000, more preferably in the range from about 800 to about 12,000, and particularly preferably in the range from about 1000 to about 10,000.

In a preferred embodiment, macromer C has a segment sequence of the formula (VIII):

b-Z-a-{c-a}$_r$-(Z-b)$_t$      (VIII)

in which r is an integer from 1 to 10, preferably from 1 to 7, and in particular from 1 to 3; t is 0 or 1, and preferably 1; a linear (c-a) chain which may or may not be terminated by a segment (b) is present (t=1); and the above preferences apply to the total number of segments (d), which are preferably bonded to a segment (b).

In another preferred embodiment, macromer C has a segment sequence of formula (IX):

b-Z-a-{c-a-(Z-b)$_t$}$_r$      (IX)

in which the sequence (c-a)-(Z-b)t hangs pendently r times on the segment (a) and may or may not be terminated by a segment (b); r is an integer from 1 to 10, preferably from 1 to 7, and in particular from 1 to 3; t is 0 or 1, and is preferably 1; Z is a segment (c) or a group $X_1$; and the above preferences apply to the total number of segments (d), which are preferably bonded to a segment (b).

Another preferred embodiment of macromer C has a segment sequence of formula (X):

b-c-{a-c}$_s$-B      (X)

in which s is an integer from 1 to 10, preferably from 1 to 7, and in particular from 1 to 3; B is a segment (a) or (b); and the above preferences apply to the number of segments (d), which are bonded to a segment (b).

Another preferred embodiment of macromer C has a segment sequence of the formula (XI):

B-(c-b)$_s$-Z-a-(b)$_t$      (XI)

in which the structures are linear; s is an integer from 1 to 10, preferably from 1 to 7, and in particular from 1 to 3; B is a segment (a) or (b); t is 0 or 1, and the above preferences apply to the number of segments (d), which are bonded to a segment (b).

The ratio of the number of segments (a) and (b) in a macromer according to the Material "C" embodiment of the invention is preferably in a range of (a):(b)=3:4, 2:3, 1:2, 1:1, 1:3 or 1:4. The total sum of segments (a) and (b) or, where appropriate, (a) and (b) and (c) is in a range from 2 to 50, preferably 3 to 30, and in particular in the range from 3 to 12.

Alkyl has up to 20 carbon atoms and can be straight-chain or branched. Suitable examples include dodecyl, octyl, hexyl, pentyl, butyl, propyl, ethyl, methyl, 2-propyl, 2-butyl or 3-pentyl.

Arylene is preferably phenylene or naphthylene, which is unsubstituted or substituted by lower alkyl or lower alkoxy, in particular 1,3-phenylene, 1,4-phenylene or methyl-1,4-phenylene; or 1,5-naphthylene or 1,8-naphthylene.

Aryl is a carbocyclic aromatic radical, which is unsubstituted or substituted by preferably lower alkyl or lower alkoxy. Examples are phenyl, toluyl, xylyl, methoxyphenyl, t-butoxyphenyl, naphthyl or phenanthryl.

A saturated bivalent cycloaliphatic group is preferably cycloalkylene, for example cyclohexylene or cyclohexylenelower alkylene, for example cyclohexylenemethylene, which is unsubstituted or substituted by one or more lower alkyl groups, for example methyl groups, for example trimethylcyclohexylenemethylene, for example the bivalent isophorone radical. The term "lower" in the context of this invention in connection with radicals and compounds, unless defined otherwise, means, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples include decylene, octylene, hexylene, pentylene, butylene, propylene, ethylene, methylene, 2-propylene, 2-butylene or 3-pentylene.

Lower alkylene is alkylene having up to 8, and particularly preferably having up to 4 carbon atoms. Particularly preferred examples of lower alkylenes are propylene, ethylene and methylene.

The arylene unit of alkylenearylene or arylenealkylene is preferably phenylene, which is unsubstituted or substituted by lower alkyl or lower alkoxy, and the alkylene unit of this is preferably lower alkylene, such as methylene or ethylene, in particular methylene. Such radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Partly fluorinated alkyl is understood as meaning alkyl in which up to 90%, preferably up to 70%, and in particular up to 50%, of the hydrogens are replaced by fluorine.

Arylenealkylenearylene is preferably phenylene-lower alkylene-phenylene having up to 8, and in particular having up to 4 carbon atoms in the alkylene unit, for example phenylenethylenephenylene or phenylenemethylenephenylene.

A monosaccharide in the context of the present invention is understood as meaning an aldopentose, aldohexose, aldotetrose, ketopentose or ketohexose.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose. Examples of a disaccharide are trehalose, maltose, somaltose, cellobiose, gentiobiose, saccharose, lactose, chitobiose, N,N-diacetylchitobiose, palatinose or sucrose. Raffinose, panose or maltotriose may be mentioned as an example of a trisaccharide. Examples of an oligosaccharide are maltotetraose, maltohexaose, chitoheptaose and furthermore cyclic oligosaccharides, such as cyclodextrins.

Cyclodextrins contain 6 to 8 identical units of α-1,4-glucose. Some examples are α-, β- and γ-cyclodextrin, derivatives of such cyclodextrins, for example hydroxypropylcyclodextrins, and branched cyclodextrins.

Macromer C can be prepared by processes known per se, for example, according the the procedures disclosed in U.S. Pat. No. 5,849,811.

Macromer D

MacromerD is a siloxane-containing macromer which is formed from a poly(dialkylsiloxane) dialkoxyalkanol having the following structure:

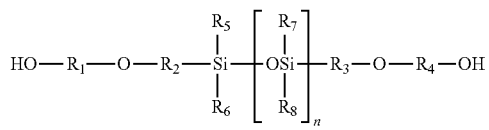

where n is an integer from about 5 to about 500, preferably about 20 to 200, more preferably about 20 to 100; the radicals $R_1$, $R_2$, $R_3$, and $R_{54}$, independently of one another, are lower alkylene, preferably $C_1$-$C_6$ alkylene, more preferably $C_1$-$C_3$ alkylene, wherein in a preferred embodiment, the total number of carbon atoms in $R_1$ and $R_2$ or in $R_3$ and $R_4$ is greater than 4; and $R_5$, $R_6$, $R_7$, and $R_8$ are, independently of one another, are lower alkyl, preferably $C_1$-$C_6$ alkyl, more preferably $C_1$-$C_3$ alkyl.

The general structure of macromer D is:

ACRYLATE-LINK-ALK-O-ALK-PDAS-ALK-O-ALK-LINK-ACRYLATE where the ACRYLATE is selected from acrylates and methacrylates; LINK is selected from urethanes and dirurethane linkages, ALK-O-ALK is as defined above ($R_1$—O—$R_2$ or $R_3$O—$R_4$), and PDAS is a poly(dialkylsiloxane).

For example, macromer D may be prepared by reacting isophorone diisocyanate, 2-hydroxyethyl (meth)acrylate and a poly(dialkylsiloxane) dialkoxyalkanol in the presence of a catalyst.

A preferred macromer D may be prepared by reacting a slight excess of isocyanatoalkyl methacrylate, especially isocyanatoethyl methacrylate (IEM), with a poly(dialkylsiloxane) dialkoxyalkanol, preferably poly(dimethylsiloxane) dipropoxyethanol, in the presence of a catalyst, especially an organotin catalyst such as dibutyltin dilaurate (DBTL). The primary resulting structure is as follows:

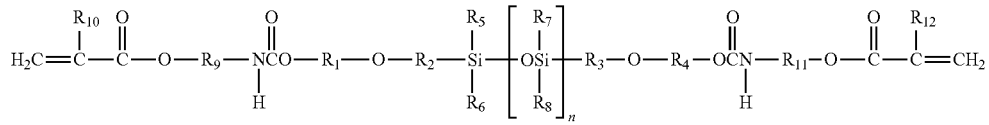

where n is an integer from about 5 to about 500; $R_1$, $R_2$, $R_3$, and $R_4$, independently of one another, are lower alkylene; $R_5$, $R_6$, $R_7$, and $R_8$ are, independently of one another, are alkyl, $R_9$ and $R_{11}$ are alkylene; and $R_{10}$ and $R_{12}$ are methyl or hydrogen.

Macromer A, Macromer B, Macromer C or Macromer D can be prepared according to the procedures described in U.S. Pat. No. 5,760,100, herein incorporated by reference in its entirety.

In accordance with the present invention, a polymerizable fluid composition can also comprise siloxane-containing monomer. Any known suitable siloxane-containing monomers can be used in the present invention. Exemplary siloxane-containing monomers include, without limitation, methacryloxyalkylsiloxanes, tristrimethylsilyloxysilylpropyl methacrylate (TRIS), 3-methacryloxy propylpentamethyldisiloxane and bis(methacryloxypropyl)tetramethyldisiloxane. A preferred siloxane-containing monomer is TRIS, which is referred to 3-methacryloxypropyltris(trimethylsiloxy) silane, and represented by CAS No. 17096-07-0. The term "TRIS" also includes dimers of 3-methacryloxypropyltris(trimethylsiloxy) silane.

In accordance with the present invention, a polymerizable fluid composition can also comprise a hydrophilic monomer. Nearly any hydrophilic monomer that can act as a plasticizer can be used in the fluid composition of the invention. Suitable hydrophilic monomers are, without this being an exhaustive list, hydroxyl-substituted lower alkyl ($C_1$ to $C_8$) acrylates and methacrylates, acrylamide, methacrylamide, (lower allyl) acrylamides and -methacrylamides, ethoxylated acrylates and methacrylates, hydroxyl-substituted (lower alkyl)acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl4,4'-dialkyloxazolin-5-one, 2- and 4-vinylpyridine, vinylically unsaturated carboxylic acids having a total of 3 to 5 carbon atoms, amino(lower alkyl)- (where the term "amino" also includes quaternary ammonium), mono(lower alkylamino)(lower alkyl) and di(lower alkylamino)(lower alkyl)acrylates and methacrylates, allyl alcohol and the like.

Among the preferred hydrophilic monomers are N,N-dimethylacrylamide (DMA), 2-hydroxyethylmethacrylate (HEMA), hydroxyethyl acrylate, hydroxypropyl acrylate, hydroxypropyl methacrylate (HPMA), trimethylammonium 2-hydroxy propylmethacrylate hydrochloride, dimethylaminoethyl methacrylate (DMAEMA), dimethylaminoethylmethacrylamide, acrylamide, methacrylamide, allyl alcohol, vinylpyridine, glycerol methacrylate, N-(1,1dimethyl-3-oxobutyl)acrylamide, N-vinyl-2-pyrrolidone (NVP), acrylic acid, methacrylic acid, and N,N-dimethyacrylamide (DMA).

A polymerizable fluid composition can also comprises a hydrophobic monomer. By incorporating a certain amount of hydrophobic monomer in a polymerizable fluid composition, the mechanical properties (e.g., modulus of elasticity) of the resultant polymer may be improved. Examples of suitable hydrophobic vinylic comonomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonyl-aminoethyl-methacrylate, isobornyl methacrylate, trifluoroethyl methacrylate, hexafluoro-isopropyl methacrylate, hexafluorobutyl methacrylate, tris-trimethylsilyloxy-silyl-propyl methacrylate, 3-methacryloxypropyl-pentamethyl-disiloxane and bis(methacryloxypropyl)-tetramethyl-disiloxane. TRIS, which may act both to increase oxygen permeability and to improve the modulus of elasticity, is a particularly preferred hydrophobic monomer.

In a preferred embodiment, a polymerizable fluid composition suitable for making an ophthalmic device will include (a) about 20 to 40 weight percent of a siloxane-containing macromer, (b) about 5 to 30 weight percent of a siloxane-containing monomer, and (c) about 10 to 35 weight percent of a hydrophilic monomer. More preferably, the siloxane-containing monomer is TRIS.

In accordance with the present invention, a polymerizable fluid composition can further comprise various components, such as cross-linking agents, initiator, UV-absorbers, inhibitors, fillers, visibility tinting agents, and the like.

Cross-linking agents may be used to improve structural integrity and mechanical strength. Examples of cross-linking agents include without limitation allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate. A preferred cross-linking agent is ethylene glycol dimethacrylate (EGDMA).

The amount of a cross-linking agent used is expressed in the weight content with respect to the total polymer and is in the range from 0.05 to 20%, in particular in the range from 0.1 to 10%, and preferably in the range from 0.1 to 2%.

Initiators, for example, selected from materials well known for such use in the polymerization art, may be included in the polymerizable fluid composition in order to promote, and/or increase the rate of, the polymerization reaction. An initiator is a chemical agent capable of initiating polymerization reactions. The initiator can be a photoinitiator or a thermal initiator.

A photoinitiator can initiate free radical polymerization and/or crosslinking by the use of light. Suitable photoinitiators are benzoin methyl ether, diethoxyacetophenone, a benzoylphosphine oxide, 1-hydroxycyclohexyl phenyl ketone and Darocur and Irgacur types, preferably Darocur 1173® and Darocur 2959®. Examples of benzoylphosphine initiators include 2,4,6-trimethylbenzoyldiphenylophosphine oxide; bis-(2,6-dichlorobenzoyl)-4-N-propylphenylphosphine oxide; and bis-(2,6-dichlorobenzoyl)-4-N-butylphenylphosphine oxide. Reactive photoinitiators which can be incorporated, for example, into a macromer or can be used as a special monomer are also suitable. Examples of reactive photoinitiators are those disclosed in EP 632 329, herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is azobisisobutyronite (AIBN).

Examples of preferred pigments include any colorant permitted in medical devices and approved by the FDA, such as D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, etc. See Marmiom DM Handbook of U.S. Colorants for a list of colorants that may be used with the present invention. A more preferred embodiment of a pigment include (C.I. is the color index no.), without limitation, for a blue color, phthalocyanine blue (pigment blue 15:3, C.I. 74160), cobalt blue (pigment blue 36, C.I. 77343), Toner cyan BG (Clariant), Permajet blue B2G (Clariant); for a green color, phthalocyanine green (Pigment green 7, C.I. 74260) and chromium sesquioxide; for yellow, red, brown and black colors, various iron oxides; PR122, PY154, for violet, carbazole violet; for black, Monolith black C-K (CIBA Specialty Chemicals).

It has been found that some classes of monomers can reduce silver ions into silver nano-particles. Examples of such monomers include without limitation acrylamide, methacrylamide, di(lower alkyl)acrylamides, di(lower alkyl) methacrylamides, (lower allyl)acrylamides, (lower allyl) methacrylamides, hydroxyl-substituted (lower alkyl) acrylamides, hydroxyl-substituted (lower alkyl) methacrylamides, and N-vinyl lactams.

Exemplary N-vinyl lactams include without limitation N-vinyl-2-pyrrolidone (NVP), N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam and N-vinyl-3,5,7-trimethyl-2-caprolactam.

A person skilled in the art will know how to determine which monomers are capable of reducing silver ions into silver nano-particles. In a preferred embodiment, a monomer capable of reducing silver ions into nano-particles is N-dimethylacrylamide (DMA) or N-vinyl-2-pyrrolidone (NVP).

In a preferred embodiment, a polymerizable fluid composition also comprises a biocompatible reducing agent.

Any suitable biocompatible reducing agents can be used in the invention. Examples of biocompatible reducing agents includes without limitation ascorbic acid and biocompatible salts thereof, and biocompatible salts of citrate.

Any known suitable soluble silver salts can be used in the present invention. Preferably, silver nitrate is used.

It has been found that a siloxane-containing macromer having hydrophilic units can stabilize silver nano-particles. A polymerizable dispersion containing silver nano-particles and a siloxane-containing macromer having hydrophilic units can be stable for a relatively long period of time, for example, at least two hours. A stable polymerizable dispersion can provide more flexibility in producing antimicrobial ophthalmic devices in which silver nano-particles are uniformly distributed. It should be understood that the addition of a hydrophilic and/or hydrophobic can also improve the stability of the polymerizable dispersion with silver nano-particles, probably due to synergy among them. For example, a polymerizable dispersion prepared from a lens formulation can be more stable than a dispersion prepared from each individual components of that lens formulation.

In a preferred embodiment of the invention, a polymerizable fluid composition comprises a stabilizer for stabilizing silver nano-particles. A "stabilizer" refers to a material which is present in a solution for preparing the nano-particles and can stabilize the resultant nano-particles. A small amount of a stabilizer present in the polymerizable dispersion can improve greatly the stability of the polymerizable dispersion. In accordance with the present invention, a stabilizer can be a polyanionic material, a polycationic material, or a polyvinylpyrrolidone (PVP).

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly(vinylbenzyltriamethylamine) (PVBT), polyaniline (PAN or PANI) (p-type doped) [or sulphonated polyaniline], polypyrrole (PPY) (p-typed doped), and poly(pyridinium acetylene).

A polycationic material used in the present invention can also include polymeric quaternary ammonium compounds (polyquats). When polyquats are used in the coating of an ophthalmic lens, they may impart antimicrobial properties to the ophthalmic lens.

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly(styrene sulfonate) (SPS) and poly(sodium styrene sulfonate) (PSSS).

The foregoing lists are intended to be exemplary, but clearly are not exhaustive. A person skilled in the art, given the disclosure and teaching herein, would be able to select a number of other useful polyionic materials including a synthetic polymer, a biopolymer or a modified biopolymer.

A preferred stabilizer is polyacrylic acid (PAA), poly(ethyleneimine) (PEI), PVP, acrylic acid, or a polyionic material having carboxy, amino and/or sulfur-containing groups.

Exemplary sulfur-containing groups include, without limitation, thiol, sulfonyl, sulfonic acid, alkyl sulfide, alkyl disulfide, substituted or unsubstituted phenyldisulfide, thiophenyl, thiourea, thioether, thiazolyl, thiazolinyl, and the like.

The amount of a stabilizer in a polymerizable fluid composition is less than 1% percent by weight, preferably less than 0.5% by weight, more preferably less than 0.1% by weight.

Alternatively, a stabilizer can be added into a polymerizable fluid composition together with soluble silver salt (e.g., a solution of $AgNO_3$ and PAA). The concentration ratio of a stabilizer to silver nano-particles is preferably from 0.1 to 10, more preferably from 0.5 to 5.

It should point out that where a stabilizer is —COOH-containing polymer (e.g., PAA), an amino-containing polycationic polymer, or a sulfur-containing polyionic polymer, the concentration of the stabilizer should be at a level below which silver ions can be reduced into silver nano-particles. If the stabilizer concentration is too high, the reduction of silver ions into silver nano-particles can be extremely slow or almost inhibited.

In accordance with the present invention, a method of the invention can also comprise a step of adding a biocompatible reducing agent while mixing thoroughly the mixture so as to facilitate the formation of the polymerizable dispersion containing silver nano-particles.

Medical devices of the invention can be made in a manner known per se from a polymerizable fluid composition by a polymerization reaction in molds for making the medical devices with which the expert is familiar. For example, an ophthalmic lens may be manufactured, generally, by thoroughly mixing the polymer composition of the present invention, applying an appropriate amount of the mixture to a lens mold cavity, and initiating polymerization. Photoinitiators, such as those commercially available photoinitiators, e.g., DAROCUR® 1173 (a photoinitator available from Ciba-Geigy Corporation), may be added to the polymer composition to aid in initiating polymerization. Polymerization may be initiated by a number of well known techniques, which, depending on the polymerizable material, may include application of radiation such as microwave, thermal, e-beam and ultraviolet. A preferred method of initiating polymerization is by application of ultraviolet radiation.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a contact lens mold.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. Nos. 4,444,711 to Schad; 4,460,534 to Boehm et al.; 5,843,346 to Morrill; and 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as quartz glass.

Thermal curing or photo curing methods can be used to curing a polymerizable composition in a mold to form an ophthalmic lens. Such curing methods are well-known to a person skilled in the art.

The invention, in another aspect, provides a method for making an antimicrobial medical device, preferably an antimicrobial ophthalmic device, more preferably an antimicrobial contact lens, even more preferably an antimicrobial extended wear lens. The method comprises the steps of: obtaining a polymerizable fluid composition comprising a siloxane-containing macromer and a soluble silver salt; forming a polymerizable dispersion comprising silver nanoparticles and having a stability of at least about 60 minutes, preferably at least about 4 hours, more preferably at least about 8 hours, even more preferably at least about 15 hours, wherein the silver nanoparticles are obtained by adding into the fluid composition at least one biocompatible reducing agent; introducing an amount of the polymerizable dispersion in a mold for making a medical device; and polymerizing the mixture in the mold to form the antimicrobial medical device containing silver nanoparticles.

In accordance with this aspect of the invention, a polymerizable fluid composition can be a solution or a solvent-free liquid or melt at a temperature below 60° C.

In a preferred embodiment, the resultant antimicrobial medical device comprises at least 10 ppm, preferably at least 25 ppm, more preferably at least 40 ppm, even more preferably at least 60 ppm silver nanoparticles.

In this aspect of the invention, the above described siloxane-containing macromers, siloxane-containing monomers, hydrophilic monomers, hydrophobic monomers, solvents, stabilizers for stabilizing silver nano-particles, soluble silver salts, cross-linking agents, initiators, UV-absorbers, inhibitors, fillers, and visibility tinting agents can be used in preparation of a polymerizable fluid composition comprising a siloxane-containing macromer and a soluble silver salt. The formulations of soft contact lenses (such as lotrafilcon A, lotrafilcon B, etafilcon A, genfilcon A, lenefilcon A, polymacon, acquafilcon A, and balafilcon) can also be used.

Any suitable biocompatible reducing agents can be used in the invention. Examples of biocompatible reducing agents includes without limitation ascorbic acid and biocompatible salts thereof, and biocompatible salts of citrate.

In accordance with this aspect of the invention, a stabilizer can be added together with the biocompatible reducing agent or before adding the biocompatible reducing agent.

The invention, in still another aspect, provides a method for making an antimicrobial medical device, preferably an antimicrobial ophthalmic device, more preferably an antimicrobial contact lens, even more preferably an antimicrobial extended wear lens. The method comprises the steps of: obtaining a stabilized-silver nano-particle solution or lyophilized stabilized-silver nano-particles; directly dispersing a desired amount of the stabilized-silver nano-particle solution or the lyophilized stabilized-silver nano-particles in a polymerizable fluid composition comprising a siloxane-containing macromer to form a polymerizable dispersion having a stability of at least about 60 minutes, preferably at least about 4 hours, more preferably at least about 8 hours, even more preferably at least about 15 hours; introducing an amount of the polymerizable dispersion in a mold for making a medical device; and polymerizing the polymerizable dispersion in the mold to form the antimicrobial medical device containing silver nanoparticles.

In a preferred embodiment, the resultant antimicrobial medical device comprises at least 10 ppm, preferably at least 25 ppm, more preferably at least 40 ppm, even more preferably at least 60 ppm silver nanoparticles.

Any known suitable methods can be used in the preparation of stabilized silver nano-particles. For example, silver ions or silver salts can be reduced by means of a reducing agent (e.g., $NaBH_4$, ascorbic acid, citrate, or the like) or of heating or UV irradiation in a solution in the presence of a stabilizer to form silver nano-particles. A person skilled in the art will know how to choose a suitable known method for preparing silver nano-particles. Then, the prepared dispersion containing stabilized silver nano-particles can be lyophilized (dry-freezed).

In accordance with this aspect of the invention, a polymerizable fluid composition can be a solution or a solvent-free liquid or melt at a temperature below 60° C.

In this aspect of the invention, the above described siloxane-containing macromers, siloxane-containing monomers, hydrophilic monomers, hydrophobic monomers, solvents, stabilizers for stabilizing silver nano-particles, soluble silver salts, cross-linking agents, initiators, UV-absorbers, inhibitors, fillers, and visibility tinting agents can be used in preparation of a polymerizable fluid composition comprising a siloxane-containing macromer and a soluble silver salt. The formulations of soft contact lenses (such as lotrafilcon A, lotrafilcon B, etafilcon A, genfilcon A, lenefilcon A, polymacon, acquafilcon A, and balafilcon) can also be used.

Any one of the above described methods of the invention can be used to prepare an antimicrobial medical device, in particular an antimicrobial ophthalmic device, which is another aspect of the invention.

The invention, in a further aspect, provides an antimicrobial ophthalmic device, preferably an antimicrobial contact lens, even more preferably an antimicrobial extended-wear contact lens. The antimicrobial medical device of the invention comprises a polymer matrix, silver-nanoparticles distributed therein and a dye or pigment distributed therein in a substantially uniform manner, wherein the polymer matrix includes a polysiloxane unit, has a high oxygen permeability characterized by a $D_k$ greater than 60 barrers and a high ion permeability characterized by an ionoflux diffusion coefficient of great than $6.0 \times 10^{-4}$ mm$^2$/min, and comprises a water content of at least 15 weight percent when fully hydrated, wherein the antimicrobial medical device exhibit at least a 5-fold reduction ($\geq 80\%$ inhibition), preferably at least a 1-log reduction ($\geq 90\%$ inhibition), more preferably at least a 2-log reduction ($\geq 99\%$ inhibition), of viable microorganisms, and wherein the dye or pigment, in combination with the color of the silver nano-particle, provides a desired color. Preferably, the antimicrobial ophthalmic device has a prolong antimicrobial activity characterized by by having at least a 5-fold reduction ($\geq 80\%$ inhibition), preferably at least a 1-log reduction ($\geq 90\%$ inhibition), more preferably at least a 2-log reduction ($\geq 99\%$ inhibition), of viable microorganisms (e.g., *Pseudomonas aeruginosa* GSU #3, or *Staphylococcus aureus* ATCC #6538) after at least 5, preferably at least 10, more preferably at least 20, even more preferably at least 30 consecutive soaking/rinsing cycles, each cycle comprising soaking/rinsing one lens in a phosphate buffered saline (PBS) for a period of time from about 24 to about 72 hours, as shown in Example.

In a preferred embodiment, an antimicrobial medical device of the invention comprises at least 10 ppm, preferably at least 25 ppm, more preferably at least 40 ppm, even more preferably at least 60 ppm silver nanoparticles.

Above described polymerizable fluid compositions can be used in the preparation of an antimicrobial ophthalmic device according to any methods of the invention. The ophthalmic lenses of the present invention preferably have a surface which is biocompatible with ocular tissue and ocular fluids during the desired extended period of contact.

In one preferred embodiment, the ophthalmic lenses of the present invention include a core material, as defined above, surrounded, at least in part, by a surface which is more hydrophilic and lipophobic than the core material. A hydrophilic surface is desirable in order to enhance the compatibility of the lens with the ocular tissues and tear fluids. As surface hydrophilicity increases, undesirable attraction and adherence of lipids and proteinaceous matter typically decreases. There are factors other than surface hydrophilicity, such as immunological response, which may contribute to deposit accumulation on the lens. Deposition of lipids and proteinaceous matter causes haze on the lens, thereby reducing visual clarity. Proteinaceous deposits may also cause other problems, such as irritation to the eye. After extended periods of continuous or intermittent wear, the lens must be removed from the eye for cleaning, i.e., deposit removal. Therefore, increased surface hydrophilicity, and concomitant reductions in deposits of biological matter, allows increased wear time.

There are a variety of methods disclosed in the art for rendering a surface of a material hydrophilic. For example, the lens may be coated with a layer of a hydrophilic polymeric material. Alternatively, hydrophilic groups may be grafted onto the surface of the lens, thereby producing a monolayer of hydrophilic material. These coating or grafting processes may be effected by a number of processes, including without limitation thereto, exposing the lens to plasma gas or immersing the lens in a monomeric solution under appropriate conditions.

Another set of methods of altering the surface properties of a lens involves treatment prior to polymerization to form the lens. For example, the mold may be treated with a plasma (i.e., an ionized gas), a static electrical charge, irradiation, or other energy source, thereby causing the prepolymerzation mixture immediately adjacent the mold surface to differ in composition from the core of the prepolymerization mixture.

A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

In a preferred embodiment, an ophthalmic lens is subjected to a plasma treatment in the presence of a mixture of (a) a $C_{1-6}$ alkane and (b) a gas selected from the group consisting of nitrogen, argon, oxygen, and mixtures thereof. In a more preferred embodiment, the lens is plasma treated in the presence of a mixture of methane and air.

In another preferred embodiment, an ophthalmic lens has an LbL coating thereon. Formation of an LbL coating on an ophthalmic device may be accomplished in a number of ways, for example, as described in U.S. Pat. Ser. No. 6,451,871 (herein incorporated by reference in its entirety) and pending U.S. patent applications (application Ser. Nos. 09/774942, 09/775104, 10/654,566), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

In accordance with a more preferred embodiment of the invention, an ophthalmic device comprises: an antimicrobial coating which comprises at least one antimicrobial agent selected from the group consisting of a polyquat which exhibits antimicrobial activity, furanones, antimicrobial peptides, isoxazolinones, and organic selenium compounds. Such medical device may exhibit antimicrobial synergy of silver and one or more antimicrobial agents and therefore may possess a higher antimicrobial efficacy and a broader spectrum of antimicrobial activities.

Any polyquats which exhibit antimicrobial activity can be used in the present invention. Exemplary preferred polyquats are those disclosed in copending U.S. patent application Ser. No. 10/287,091 filed Nov. 4, 2002, entitled "Medical Devices Having Antimicrobial Coatings thereon", herein incorporated by reference. The methods for applying such coating onto an ophthalmic device have been described fully in the copending U.S. patent application Ser. No. 10/287,091 and are incorporated by reference in its entirety.

Any antimicrobial peptides can be used in the present invention. Exemplary antimicrobial peptides include without limitation Cecropin A melittin hybrid, indolicidin, lactoferricin, Defensin 1, Bactenecin (bovin), Magainin 2, functionally equivalent or superior analogs thereof, mutacin 1140, and mixtures thereof.

Any furanones, which exhibit antimicrobial activity, can be used in the present invention. Exemplary preferred furanones are those disclosed in PCT published patent applications WO01/68090A1 and WO01/68091 A1, incorporated herein by reference in their entireties.

Any organic selenium compounds, which exhibit an antimicrobial activity, can be used in the present invention. Examples of antimicrobial organic selenium compounds includes without limitation those disclosed in U.S. Pat. Nos. 5,783,454, 5,994,151, 6,033,917, 6,040,197, 6,043,098, 6,043,099, 6,077,714, herein incorporated by reference in their entireties.

Any isoxazolinones, which exhibit an antimicrobial activity, can be used in the present invention. Examples of isoxazolinones include without limitation those disclosed in U.S. Pat. Nos. 6,465,456 and 6,420,349 and U.S. patent application Ser. No. 2002/0094984, herein incorporated by reference in their entireties.

An antimicrobial agent can be covalently attached to a medical device by first functionalizing the surface of a preformed medical device to obtain function groups and then covalently attaching an antimicrobial agent. Surface modification (or functionalization) of a medical device is well known to a person skilled in the art. Any known suitable method can be used.

For example, the surface modification of a contact lens includes, without limitation, the grafting of monomers or macromers onto polymers to make the lens biocompatible, wherein monomers or macromers contain functional groups, for example, such as hydroxyl group, amine group, amide group, sulfhydryl group, —COOR (R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, epoxy.

It is well known in the art that a pair of matching functional groups can form a covalent bond or linkage under known reaction conditions, such as, oxidation-reduction conditions, dehydration condensation conditions, addition conditions, substitution (or displacement) conditions, 2+2 cyclo-addition conditions, Diels-Alder reaction conditions, ROMP (Ring Opening Metathesis Polymerization) conditions, vulcanization conditions, cationic crosslinking conditions, and epoxy hardening conditions. For example, an amino group is covalently bondable with aldehyde (Schiff base which is formed from aldehyde group and amino group may further be reduced); an hydroxyl group and an amino group are covalently bondable with carboxyl group; carboxyl group and a sulfo group are covalently bondable with hydroxyl group; a mercapto group is covalently bondable with amino group; or a carbon-carbon double bond is covalently bondable with another carbon-carbon double bond.

Exemplary covalent bonds or linkage, which are formed between pairs of crosslinkable groups, include without limitation, ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide.

Another example is amination of the surface of a medical device. If the surface of a core material has hydroxy groups, the medical device may be placed in a bath of an inert solvent, such as tetrahydrofuran, and tresyl chloride. The hydroxy groups on the surface are then tresylated. Once tresylated, the surface may be aminated in a water solution of ethylene diamine, which results in bonding the group —NH—CH$_2$—CH$_2$—NH$_2$ to the carbon atom thereon. Alternatively, for example, a contact lens made from a hydrogel, can be dipped into or sprayed with a solution containing a diaziridine compound, which is subsequently attached covalently to the surface of the contact lens via a thermal process, so as to functionalize the contact lens. Such functionalized lenses can be used in covalently attaching of a layer of antimicrobial agents.

Antimicrobial agents can be bound covalently to the coating (e.g., an LbL coating) of an antimicrobial medical device of the invention, through the reactive sites of the coating. For example, an LbL coating containing reactive sites (e.g., amino groups, —COOH groups, etc) is applied to an antimicrobial medical device of the invention and then a layer of at least one antimicrobial agent is covalently attached to some of those reactive sites.

This may be either a direct reaction or, preferably, a reaction in which a coupling agent is used. For example, a direct reaction may be accomplished by the use of a reagent of reaction that activates a group in the LbL coating or the antimicrobial agent making it reactive with a functional group on the antimicrobial agent or LbL coating, respectively, without the incorporation of a coupling agent. For example, one or more amine groups on an LbL coating may be reacted directly with isothiocyanate, acyl azide, N-hydroxysuccinimide ester, sulfonyl chloride, an aldehyde, glyoxal epoxide, 25 carbonate, aryl halide, imido ester, or an anhydride group in an antimicrobial agent.

Alternatively, coupling agents may be used. Coupling agents useful for coupling antimicrobial agent to the LbL coating of a medical device include, without limitation, N. N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl)carbodiimide, diisopropyl carbodiimide, or mixtures thereof. The carbodiimides also may be used with N-hydroxysuccinimide or N-hydroxysulfosuccinimide to form esters that can react with amines to form amides.

Amino groups also may be coupled to the LbL coating by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl) suberate, disuccinimidyl tartarate and the like, imidoesters, including, without limitation, dimethyl adipimate, difluorobenzene derivatives, including without limitation 1,5-difluoro-2, 4 dinitrobenzene, bromofunctional aldehydes, including without limitation gluteraldehyde, and his epoxides, including without limitation 1,4-butanediol diglycidyl ether. One ordinarily skilled in the art will recognize that any number of other coupling agents may be used depending on the functional groups present in the LbL coating.

The previous disclosure will enable one having ordinary skill in the art to practice the invention. In order to better enable the reader to understand specific embodiments and the advantages thereof, reference to the following examples is suggested.

EXAMPLE 1

Unless otherwise stated, all chemicals are used as received.
Synthesis of Macromer 51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 meq/g (theory: 1.35 meq/g).

202 g of the a,co-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 100 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g). 13.78 g (88.9 mmol) of 2-isocyanatoethyl methacrylate (IEM) are added under argon to 247 g of the α,σ-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

Formulations

The above prepared siloxane-containing macromer is use in preparation of two formulations used in the following examples. Each components and its concentration are listed in Table 1.

TABLE 1

| Formulation | Macromer | TRIS | DMA | Darocure ® 1173 | Ethanol |
|---|---|---|---|---|---|
| I* | 37.4 | 15.0 | 22.5 | 0.3 | 24.8 |
| II** | 25.9 | 19.2 | 28.9 | 1 | 25 |

*Unless otherwise indicated in the text, Formulation I does not contain tinting agents (colorants).
**Formulation II contains about 50 ppm of copper phthalocyanine (CuP).

Lenses are extracted with isopropanol (isopropyl alcohol) for at least 2 hours and then subjected plasma treatment according to procedures described in published U.S. patent application Ser. No. 2002/0,025,389 to obtain plasma coatings. Oxygen and ion permeability measurements are carried out with lenses after extraction and plasma coating.

Oxygen Permeability and Transmissibility Measurements.

The oxygen permeability of a lens and oxygen transmissibility of a lens material is determined according to a technique similar to the one described in U.S. Pat. No. 5,760,100 and in an article by Winterton et al., (The Cornea: Transactions of the World Congress on the Cornea 111, H. D. Cavanagh Ed., Raven Press: New York 1988, pp273-280), both of which are herein incorporated by reference in their entireties. Oxygen fluxes (J) are measured at 34° C. in a wet cell (i.e., gas streams are maintained at about 100% relative humidity) using a Dk1000 instrument (available from Applied Design and Development Co., Norcross, Ga.), or similar analytical instrument. An air stream, having a known percentage of oxygen (e.g., 21%), is passed across one side of the lens at a rate of about 10 to 20 cm$^3$/min., while a nitrogen stream is passed on the opposite side of the lens at a rate of about 10 to 20 cm$^3$/min. A sample is equilibrated in a test media (i.e., saline or distilled water) at the prescribed test temperature for at least 30 minutes prior to measurement but not more than 45 minutes. Any test media used as the overlayer is equilibrated at the prescribed test temperature for at least 30 minutes prior to measurement but not more than 45 minutes. The stir motor's speed is set to 1200±50 rpm, corresponding to an indicated setting of 400±15 on the stepper motor controller. The barometric pressure surrounding the system, $P_{measured}$, is measured. The thickness (t) of the lens in the area being exposed for testing is determined by measuring about 10 locations with a Mitotoya micrometer VL-50, or similar instrument, and averaging the measurements. The oxygen concentration in the nitrogen stream (i.e., oxygen which diffuses through the lens) is measured using the DK1 000 instrument. The apparent oxygen permeability of the lens material, $Dk_{app}$, is determined from the following formula:

$$Dk_{app} = Jt/(P_{oxygen})$$

where J=oxygen flux [microliters O$_2$/cm$^2$ -minute]
$P_{oxygen} = (P_{measured} - P_{water} \text{vapor}) = (\%O_2 \text{ in air stream}) $ [mm Hg]=partial pressure of oxygen in the air stream
$P_{measured}$=barometric pressure (mm Hg)
$P_{water}$ vapor=0 mm Hg at 34° C. (in a dry cell) (mm Hg)
$P_{water}$ vapor=40 mm Hg at 34° C. (in a wet cell) (mm Hg)
t=average thickness of the lens over the exposed test area (mm) where $Dk_{app}$ is expressed in units of barrers.

The oxygen transmissibility (Dk/t) of the material may be calculated by dividing the oxygen permeability ($Dk_{app}$) by the average thickness (t) of the lens.

Ion Permeability Measurements.

The ion permeability of a lens is measured according to procedures described in U.S. Pat. No. 5,760,100 (herein incorporated by reference in its entirety. The values of ion permeability reported in the following examples are relative ionoflux diffusion coefficients ($D/D_{ref}$) in reference to a lens material, Alsacon, as reference material. Alsacon has an ionoflux diffusion coefficient of 0.314×10$^{-3}$ mm$^2$/minute.

EXAMPLE 2

This example illustrates unexpected discoveries that, without adding any extra reducing agent, one can obtain a relatively stable polymerizable dispersion containing silver nano-particles (Ag NP) by simply adding silver salt (e.g. AgNO$_3$, or AgClO$_4$) into a polymerizable composition comprising a siloxane-containing macromer with hydrophilic units, a siloxane-containing monomer, a hydrophilic monomer capable of reducing silver ions into silver nano-particles.

Addition of AgNO$_3$ in Formulation I

A silver nitrate solution is added into a volume of formulation I to make the concentration of silver nitrate equal to about 50 ppm. Before mixing, both silver nitrate and formulation I are clear/colorless in appearance under the examination of naked eyes. However, formulation I turns into yellowish appearance after adding silver nitrate therein, indicating the formation of silver nano-particles. The formation of silver nano-particles is also confirmed by UV spectroscopy with absorption peaks around 420-430 nm, a characteristic of silver nano-particles. When monitoring the UV absorption spectrum of the formulation I after adding silver nitrate, the intensity of a UV absorption peak around 430 nm is observed to increase with mixing time but reaches a plateau in about 8 hours, as shown in Table 2. Silver nano-particles are formed when adding 50 ppm of silver nitrate into the formulation I.

TABLE 2

| | Time (minutes) | | | | | | | | |
|---|---|---|---|---|---|---|---|---|---|
| | 10 | 30 | 60 | 240 | 480 | 720 | 1800 | 3540 | 5160 |
| Peak position (nm) | 430 | 430 | 431 | 435 | 427 | 425 | 417 | 420 | 421 |
| Peak Intensity | 0.213 | 0.342 | 0.526 | 0.700 | 0.834 | 0.891 | 0.881 | 0.838 | 0.879 |

In another experiment, a silver nitrate solution is added into a volume of formulation I to make the concentration of silver nitrate equal to about 610 ppm. When monitoring the UV absorption spectrum of the lotrafilcon A formulation after adding silver nitrate, it is observed that the intensity of a UV absorption peak around 430 nm increases from about 1.1 at about 30 minutes, to about 1.34 at about 90 minutes, and to about 1.34 at about 180 minutes. Silver nano-particles are formed when adding 610 ppm of silver nitrate into formulation I.

The absorption peak position and peak intensity depends on the concentration of added silver salt. when the concentration of $AgNO_3$ increased from about 80ppm, to 800 ppm, to 1600 ppm, the peak position changes from 423 nm, to 430 nm and then to 433 nm, respectively.

Addition of $AgClO_4$ in Formulation I

A silver perchlorate ($AgClO_4$) solution is added into a volume of formulation I to obtain a concentration of 60 ppm of silver perchlorate ($AgClO_4$). When monitoring the UV absorption spectrum of the formulation I after adding silver perchlorate ($AgClO_4$), it is observed that the intensity of a UV absorption peak around 430 nm increases with mixing time but reaches a plateau in about 8-10 hours, as shown in Table 3. Silver nano-particles are formed when adding 60 ppm of silver perchlorate ($AgClO_4$) into the lotrafilcon A formulation.

TABLE 3

| | Time (minutes) | | | | | | | | |
|---|---|---|---|---|---|---|---|---|---|
| | 10 | 30 | 60 | 240 | 480 | 720 | 1800 | 3540 | 5160 |
| Peak position (nm) | 430 | 430 | 431 | 438 | 427 | 425 | 417 | 420 | 421 |
| Peak Intensity | 0.242 | 0.394 | 0.576 | 0.875 | 0.887 | 0.965 | 0.989 | 0.857 | 0.950 |

Extremely Slow Formation of Ag NP in Ethanol 0.0397 g $AgNO_3$ solid is added into 20 ml of ethanol at room temperature. It took almost 1 hour to completely dissolve $AgNO_3$ in ethanol under vigorous stirring. No UV peak is observed after 5 hours. After 5 days, a tiny absorption peak around 367 nm is observed, indicating the formation of some silver nano-particles (Ag-NPs). To speed up the reduction of $Ag^+$ to $(Ag^0)_n$, reducing agent (in this case, sodium borohydride, $NaBH_4$) and stabilizer (polyacrylic acid, PAA, Mw=2000) is added into the ethanol solution. It turned out that reducing process is still very slow with added reducing agent. After 6 days, a tiny peak around 365 nm is observed. Results indicate that Ag NPs can be formed in an extremely slow manner in ethanol.

Formation of Unstable Ag NP in Dimethyl Acrylamide (DMA)

When adding silver nitrate (0.01113 g or 0.1113 g) into DMA (50 ml), its color changes from colorless to yellowish, indicating the formation of silver nano-particles. The formation of silver nano-particles is also confirmed by UV spectroscopy, as listed in Table 4. However, the silver nano-particles can not form a stable dispersion in DMA. Instead, the silver nano-particles precipitate on the wall of the container and forms a "silver mirror within a hour"

TABLE 4

| | Time (minutes) | | | |
|---|---|---|---|---|
| | 40 | 60 | 90 | 120 |
| Peak position (nm) | 430 | 430 | 431 | 435 |
| Peak Intensity[1] | 0.657 | 1.191 | 1.421 | 1.406 |
| Peak position (nm) | 0.213 | 0.342 | 0.526 | 0.700 |
| Peak Intensity[2] | 1.509 | 1.583 | 1.397 | 1.299 |

[1]Adding 0.01113 g $AgNO_3$ in 50 ml of DMA, equivalent of 222 ppm of $AgNO_3$
[2]Adding 0.1113 g $AgNO_3$ in 50 ml of DMA, equivalent of 2226 ppm of $AgNO_3$ Formation of Ag NP in N-vinylpyrrolidone (NVP)

When 0.1113 gram of silver nitrate is added into 10 ml of NVP (about 11130 ppm of $AgNO_3$) at room temperature, the color of NVP changes from clear to yellow after about 10 min, indicating the formation of silver nano-particles. This is confirmed by a UV absorption peak at 440 nm. At 3 hours the absorption intensity is about 0.10. After 24 hours at 4° C., the absorption intensity increases to about 0.19. No precipitation of particles is observed after about 24 hours.

No Formation of Ag NP in HEMA

When adding 0.0015 gram of silver nitrate in 30 ml of hydroxyethyl methacrylate (HEMA) (50 ppm of $AgNO_3$), no color change is observed.

No Formation of Ag NP in TRIS

Qualitatively, when adding silver nitrate in TRIS, no color change is observed.

Formation of Unstable Ag-NP in a Mixture of DMA and TRIS

When adding 197 or 1310 ppm of silver nitrate into 1:1 (volume ratio) mixtures of DMA and TRIS, the formation of silver nano-particles is observed from the color change. Where $AgNO_3$ concentration is 197 ppm, the color of the solution changes from clear to gold yellow, then to brown yellow. After 3 hr, deposit is found on the wall of the container. Where $AgNO_3$ concentration is 1310 ppm, after one hour, the color changes to black and deposit is found on the wall of the container.

Formation of Ag-NP in a Mixture of DMA and Siloxane-Containing Macromer

When adding silver nitrate in 1.66:1 (volume ratio) mixtures of DMA and macromer prepared in Example 1, the formation of silver nano-particles is observed from the color change. The concentration of silver nitrate in this experiments ranges from about 84 ppm to 840 ppm. The color of the solution changes from clear to yellow after about 20 minutes. The mixture is stirred for about 5 hours. About one hour after stopping stirring, some deposit can be found.

Formation of Ag-NP in a Siloxane-Containing Macromer Solution

Qualitatively, when adding silver nitrate in a macromer (prepared in Example 1) solution, there is no immediate color change from the macromer solution. When observed again on $2^{nd}$ day (after about 24 hour), the slight yellow color of the macromer solution does indicate the formation of silevr nano-partilces. Some deposit can be found after two days.

EXAMPLE 3

Dispersion of Nano-Sized Activated Silver Powder in Formulation I.

To test if the nanosize activated silver powder (99.9+% Ag, from Aldrich) can be dispersed evenly (uniformly) in formulation I, an appropriate amount of silver powder is added directly into a volume of formulation to make up a solution with 500 ppm of silver powder. The nanosize activated silver powder does not dissolve in the formulation. Stirring or sonication is used to help the dispersion. After more than 1 hr of stirring, the solution appears clear with gray particles suspended within the solution. Some of the gray particles can also be seen on the stirring bar. In about 10 minutes after the stirring is stopped, gray particles are seen on the stirring bar and on the bottom of the container. In the case of sonication, the solution become cloudy after 30 minutes of sonication at 0° C. In about 20 minutes after the sonication is stopped, gray particles are seen in the bottom of the container. These experiments indicates that nanosize activated silver powder can not be dispersed in formulation I to form a stable dispersion (i.e., precipitation of particles occurs in less than 30 minutes) and that sonication may cause some partial polymerization of formulation I. Unstable polymerizable dispersion containing silver nanoparticles may not be suitable for production of antimicrobial contact lenses comprising siver nano-particles uniformly distributed therein.

EXAMPLE 4

Lenses made from Non-Degassed Formulations with 50 ppm of $AgNO_3$ Added

A polymerizable dispersion is prepared by adding calculated amount (50 ppm) of silver nitrate into a calculated amount of formulation I. The mixture of formulation I with silver salt is stirred for 1 hr at room temperature to form silver nano-particles before making contact lenses by means of molding in polypropylene molds. An amount of the polymerizable dispersion with silver nano-particles is introduced into each polypropylene molds and cured for 30 minutes under UV light to form contact lenses. The lenses are then extracted in isopropyl alcohol (IPA) overnight, then packaged and autoclaved in phosphate buffered saline.

All lenses prepared as described above are transparent with a very light yellowish hue. The lenses show a UV absorption peak around 400 nm, characteristic of Ag NP. The intensity of the peak is about 0.03 absorption unit per lens. The peak (peak position and peak intensity) is stable over time. The refractive index of the lenses is measured to be 1.427, which is the same value as lenses made from formulation I without Ag NP therein.

EXAMPLE 5

Lenses made from Non-Degassed Formulations with 5000 ppm of $AgNO_3$ Added

A polymerizable dispersion is prepared by adding a calculated amount (5000 ppm) of silver nitrate into a calculated amount of formulation 1. The mixture of formulation I with silver salt (5000 ppm) is stirred for 1 hr at room temperature before making contact lenses by means of molding in polypropylene molds. An amount of the mixture is introduced into each polypropylene molds and cured for 60 minutes under UV light to form contact lenses. The lenses are then extracted in isopropyl alcohol (IPA) overnight, then packaged and autoclaved in phosphate buffered saline.

All contact lenses prepared as described above are dark brown in color due to high concentration of silver nanoparticles. The lenses show a UV absorption peak at about 404 nm, characteristic of Ag NP. The intensity of the peak is above 1.2 absorption unit per lens.

EXAMPLE 6

Lenses made from Degassed Formulations with 50 ppm of Added $AgNO_3$

A polymerizable dispersion of silver nitrate is prepared by adding calculated amount (50 ppm) of silver nitrate into a calculated amount of formulation I. The mixture of formulation I and 50 ppm of silver salt is stirred for 1 hr before being degassed. Then the mixture containing silver is degassed to remove oxygen from the mixture. An amount of the degassed mixture is introduced into each polypropylene molds in a nitrogen glove box and cured under UV light to form contact lenses. The lenses are then extracted in IPA, then packaged and autoclaved in phosphate buffered saline.

The lenses are transparent with a very light yellowish hue. The lenses show a UV absorption peak at about 400 nm, characteristic of Ag NP. The refractive index of the lenses is measured to be 1.4257, which is the same value as the lotrafilcon A lenses without Ag NP therein.

The ion permeability (IP) of the lenses is measured to be 1.20. Control lenses made from formulation I without silver nano-particles normally have an IP value of about 1.0 or higher. These results indicate that the presence of silver nano-particles formed in situ in a lens formulation containing 50 ppm of $AgNO_3$ does no have adverse effects on the ion permeability of lenses.

The oxygen permeability (Dk) of the lenses is measured to be 109.5 barrer.

EXAMPLE 7

Lenses made from Degassed Formulations with 500 ppm of Added $AgNO_3$

A polymerizable dispersion 500 ppm of silver nitrate is prepared by adding a calculated amount (500 ppm) of silver nitrate into a calculated mount of formulation I. The mixture of formulation with silver salt is stirred for 1 hr before being degassed. Then the mixture containing silver is degassed to remove oxygen from the mixture. An amount of the degassed mixture containing silver is introduced into each polypropylene molds in a nitrogen glove box and cured under UV light to form contact lenses. The lenses are then extracted in IPA, then packaged and autoclaved in phosphate buffered saline.

The lenses are transparent with a very light yellowish hue. The lens show a UV absorption peak at about 400 nm, characteristic of Ag NP. The refractive index of the lens is measured to be 1.4259, which is the same value as control lenses without Ag NP therein.

The ion permeability (IP) of the lenses is measured to be 1.508. Control lenses without Ag NP therein normally have an IP value of higher than 1.0. These results indicate that the presence of silver nano-particles formed in situ in formulation I containing 500 ppm of $AgNO_3$ does no have adverse effects on the ion permeability of lenses.

The oxygen permeability (Dk) of the lenses is measured to be 108.66 barrer.

EXAMPLE 8

Formation of Ag NP in Formulation I in the Presence of a Stabilizer.

When silver nitrate is added directly to formulation I, the formed silver nano-particles are usually stable only up to about two or more hours depending on silver nitrate concentration. For examples, for 100 ppm silver nitrate in formulation I, severe precipitation of particles can be found after overnight. However, when PAA as stabilizer is used appropriately, the stability of the silver nano-particles in formulation I is significantly increased to at least 3 days for a mixture of formulation I with 100 ppm of silver nitrate.

Polyacrylic acid (PAA) can function as a stabilizer of silver nanoparticles in aqueous medium to prevent the aggregation of silver nano-particles. It is discovered that when a small amount of PAA is added into formulation I, the stability of the silver nanoparticles in the formulation is further improved. The order of adding PAA is important. The PAA can be added alone into the formulation, or the mixture of PAA and silver salt can be added into the formulation, or the mixture of DMA+PAA+silver salt can be added into the formulation. The ratio of DMA/PAA/AgNO$_3$ could be varied from 1/1/1 to x/y/1, here x can be greater or small than 1, y can be greater or smaller than 1. Preferably, x is between 0.1 and 10, y is between 0.1 and 10, more preferably, x is between 5 and 0.5, and y is between 0.5 and 5. The concentration of PAA in the formulation can be between 1 ppm and 500 ppm, more preferably between 1 and 300 ppm.

EXAMPLE 9

Formation of Ag NP in Formulation II

A polymerizable dispersion is prepared by adding a calculated amount (50 ppm) of silver silver nitrate) into a calculated mount of formulation II. The mixture of formulation II with silver salt is stirred for 1 hr before being cast. The mixture is then cast into polypropylene molds at ambient condition and cured under UV light for 30 min to form lenses. The lenses are then extracted in IPA, then packaged and autoclaved in phosphate buffered saline.

The lenses are transparent with a very very light bluish hue. The lens show a UV absorption peak at about 400 nm, characteristic of Ag NP.

EXAMPLE 10

Preparation of Ag NP-Containing Polymerizable Dispersion by Mixing Preformed Ag NP into Formulation I Stabilized-Ag nano-particles (Ag NP) are prepared as follows. 1 mL of 0.01 M AgNO$_3$ is mixed with 0.5 mL of 4% (by weight) PAA solution. PAA functions as a stabilizer for Ag NP. The mixture is then keep at 0° C. using ice-water mixture. Ice cold water is used to prepare 98.5 mL of 1 mM NaBH$_4$ solution, which is also kept in 0° C. using ice-water mixture. The mixture of AgNO$_3$ and PAA is then added rapidly into 98.5 mL of 1 mM NaBH$_4$ solution with vigorous stirring. The beaker is surrounded by ice to keep at about 0° C.

It should be understood that the Ag$^+$ reduction reaction can be carried at various temperatures, for example, at any temperature between 0° C. and elevated temperature, preferably between 0° C. and the room temperature, and for a period of time from a few minutes to 24 hours or longer. PAA with different molecular weight can be used. It should be also understood that UV irradiation, heating, or hydrogen can also be used to reduce Ag+ to form Ag nano-particles.

Direct adding aqueous stabilized-Ag NP solution into formulation I causes the formulation to become cloudy and therefore is not feasible for making contact lenses.

It is found that a lyophilized stabilized Ag silver nanoparticles can be successfully dispersed in formulation I. The PAA-stabilized Ag NP dispersion is lyophilized (i.e., freeze dried) to obtain lyophilized stabilized-Ag nano-particles, which appear a color of brown or black. Re-suspending the stabilized-Ag NP directly in formation I leads to a quasi-homogeneous solution which is yellowish in color and has a UV absorption around 440 nm. This provides an alternative and effective way for preparing a polymerizable dispersion which contains Ag NP.

EXAMPLE 11

Antimicrobial Activity Assay

Antimicrobial activity of a contact lens with or without silver nanoparticles in the lenses of the invention is assayed against *Pseudomonas aeruginosa* GSU #3, which is isolated from a corneal ulcer. Bacterial cells of *Pseudomnas aeruginosa* GSU #3 is stored in a lyophilized state. Bacteria are grown on an Tryptic Soy agar slant for 18 hours at 37° C. The cells are harvested by centrifugation and washed twice with sterile, Delbeco's phosphate buffered saline. Bacterial cells are suspended in PBS and adjusted to Optical Density of 10$^8$ cfu. The cell suspension is serially diluted to 10$^3$ cfu/ml.

Antimicrobial activity of some contact lenses with or without silver nanoparticles in the lenses of the invention is also assayed against *Staphylococcus aureus* ATCC #6538. Bacterial cells of *S. aureus* #6538 is stored in a lyophilized state. Bacteria are grown on an Tryptic Soy agar slant for 18 hours at 37° C. The cells are harvested by centrifugation and washed twice with sterile, Delbeco's phosphate buffered saline. Bacterial cells are suspended in 1/20 th strength Tryptic Soy Broth (TSB) and adjusted to Optical Density of 10$^8$ cfu. The cell suspension is serially diluted to 10$^3$ cfu/ml in 1/20th strength TSB.

Lenses having silver in them are tested against the control lenses (i.e., without silver). 200 µl of from about 5×10$^3$ to 1×10$^4$ cfu/ml of *P. aeruginosa* GSU #3 or *S. aureus* #6538 is placed on the surface of each lens. Incubate at 25° C. for 24 hours. Aspirate 50 µl out of the lens, serially dilute and plate out on agar plates to determine the microbial load of each lens. At 24 hours, colony counts are taken.

In-vitro Zone of Inhibition Test

Tryptic Soy Agar (TSA) slants are inoculated with *Pseudomonas* challenge organisms and are incubated 18-24 hours at 37° C. with 5% CO$_2$. Following incubation the TSA slants are flooded with DPBS to suspend the cells. The cell suspension is centrifuged and the supernatant decanted. The cell pellet is washed once via re-suspension in DPBS, centrifugation and decanting. The final washed cell pellet is then re-suspended in DPBS and the suspension density adjusted to approximately 1×10$^8$ CFU/mL using a spectrophotometer. The cell suspension is serially diluted in PBS to a final concentration of approx. 5×10$^5$ CFU/mL. TSA plates are seeded with *Pseudomonas* by spread plating 0.1 mL of the above suspension and allowing the plates to dry for 15 minutes at ambient temperature.

Each TEST or CONTROL lens is aseptically transferred to the surface of the TSA plates previously seeded with *Pseudomonas* challenge organism. If necessary, the lenses are aseptically cut along their radius (pinwheel fashion) in order to facilitate full and direct contact with the plate surface. The plates are then incubated at 37° C. w/o CO$_2$ for approximately 18-24 hours and observed for growth periodically for 72 hours.

Following incubation the Pseudomonas challenge organism should exhibit confluent growth over the entire plate surface. A "clear zone" observed surrounding the lens indicates leaching of microbicidal agent(s) from the lens into the surrounding media in sufficiently high concentration to inhibit the growth of the Pseudomonas challenge organism. The diameter of this zone can be measured as an indication of the relative degree of inhibition.

in-vitro Antimicrobial Activity of Lenses from Example 4

Antimicrobial activity of a contact lens with silver nanoparticles is assayed against *Pseudomonas aeruginosa* GSU #3 according to the procedure described above. The lenses with silver nano-particles show antimicrobial activity, characterized by at least 88% inhibition of viable cells as compared to the control lenses. Averaged CFU/lens for control lenses (without silver nanoparticles) is about 2.9×10$^4$.

No zone of inhibition is found, which indicated no leaching of high concentration of silver within the test period of time.

in-vitro Antimicrobial Activity of Lenses from Example 6

Antimicrobial activity of a contact lens with silver nanoparticles is assayed against *Pseudomonas aeruginosa* GSU

3 according to the procedure described above. The lenses with silver nano-particles show antimicrobial activity, characterized by 100% inhibition of viable cells as compared to the control lenses. Averaged CFU/lens for control lenses (without silver nanoparticles) is about $2.9 \times 10^4$ No zone of inhibition is found, which indicated no leaching of high concentration of silver within the test period of time.
in-vitro Antimicrobial Activity of Lenses from Example 7

Antimicrobial activity of a contact lens with silver nano-particles is assayed against *Pseudomonas aeruginosa* GSU #3 according to the procedure described above. The lenses with silver nano-particles show antimicrobial activity, characterized by 100% inhibition of viable cells as compared to the control lenses. Averaged CFU/lens for control lenses (without silver nanoparticles) is about $2.9 \times 10^4$.

No zone of inhibition is found, which indicated no leaching of high concentration of silver within the test period of time.
in-vitro Antibacterial Activity of Lenses from Example 9

Antimicrobial activity of a contact lens with silver nano-particles is assayed against *Pseudomonas aeruginosa* GSU #3 according to the procedure described above. The lenses with silver nano-particles show antimicrobial activity, characterized by 100% inhibition of viable cells as compared to the control lenses. Averaged CFU/lens for control lenses (without silver nanoparticles) is about $2.9 \times 10^4$.

EXAMPLE 12

Control the Color of Silver Nanoparticles Solutions

Normally, yellow is the color for silver nano-particles solutions formed either in aqueous solution using reducing agent (e.g. $NaBH_4$) or in formulation I or II. It is unexpected discovered that colors other than yellow can be generated by exposing a $PAA-AgNO_3$ mixture solution to a certain UV treatment.
1. Aqua blue silver nano-particle solution:
A solution of $PAA-AgNO_3$ mixture with 1:1 molar ratio of —COOH and $AgNO_3$ is prepared by dissolve calculated amount of PAA and $AgNO_3$ into appropriate volume of water. The pH of the solution is about 3.3-3.4 for a 10 mM solution. The solution is clear with no color. Then the solution is exposed to a LQ-400 Grobel lamp whose UV spectrum covers from 250 nm to 660 nm. The exposure time varies from 10 sec to 180 sec. It is discovered that at 35 sec exposure, the solution remains clear; after 50 sec exposure, the solution turned into aqua blue; after 180 sec exposure, the solution remains aqua blue. The blue color cannot be produced when the $PAA-AgNO_3$ mixture solution is exposed to a fluorescent tube with a UV spectrum of 350 to 440 nm. It is also discovered that the blue color disappear when the pH of the solution is adjusted to 2.5 using nitric acid.
2. Pink silver nano-particle solution
Another unexpected and interesting discovery is that when the pH of the solution is first adjusted to 5.0, the solution turned from clear to pink when exposed to a LQ-400 Grobel lamp for 30 sec or longer. In addition the color progressed from light pink to medium pink and then to dark pink when the exposure time increased from 30 sec, to 65 sec and then to 120 sec.
3. Green silver nano-particle solution
When adding a drop of 1 mM NaBH4 solution to 10 mM of $PAA-AgNO_3$ (1:1) mixture solution, the solution turned from clear to light yellow. Interestingly, the solution then turned into green color after exposed for 65 sec to a LQ-400 Grobel lamp.

EXAMPLE 13

Preparation of Clear and/or Visitinted Lenses from Formulation I Containing Silver Nano-Particles and Colorant.

Normally, lenses containing silver nano-particles may have a yellowish tint or appear yellowish depending on the concentration of silver in the lenses. It is discovered that the yellowish tint or color can be compensated by using a colorant. One example is to use carbazole violet, an FDA approved pigment used in color contact lenses, for examples, Freshlook color contact lenses.

Lenses with different color appearance are made from mixtures of formulation I with variable concentrations of carbazole violet. Firstly, formulation I containing silver nao-particles are prepared according the procedure described in Example 4. The formulation with silver nano-particles are usually yellowish in color. Secondly, the color of the yellowish dispersion is adjusted by adding either a carbazole violet stock solution (~2% carbazole violet in hydroxyethyl methacrylate (HEMA)) or carbazole violet powder. Then an amount of the dispersion with carbazole violet and silver nano-particles is introduced into each polypropylene molds and cured for 5 minutes under UV light to form contact lenses. The lenses are then extracted in isopropyl alcohol (IPA), then packaged and autoclaved in phosphate buffered saline.

As listed in Table 5, clear and visited lenses containing silver nano-particles are successfully prepared.

TABLE 5

| $[AgNO_3]$ ppm | [Carbazole violet] ppm | Color of formulation | Color of lens | Carbzaole violet source |
|---|---|---|---|---|
| 50 | 0 | yellow | yellowish tint | / |
| 50 | 20 | Lilac purple | clear | Stock solution |
| 100 | 50 | purple | light purple tint | Stock solution |
| 100 | 100 | dark purple | purple tint | Stock solution |
| 100 | 45 | dark purple | pink tint | powder |
| 100 | 90 | dark purple | purple tint | powder |

EXAMPLE 14

All of the lenses in this example are cast at ambient condition, UV cured and IPA extracted.
Control Lenses made from Formulation II without Silver Nano-Particles Control lenses are prepared from formulation II without adding any silver salt or silver nano-particles. An amount of formulation II is introduced into each polypropylene molds and cured for 60 minutes under UV light to form contact lenses. The lenses are then extracted in isopropyl alcohol (IPA), then packaged and autoclaved in phosphate buffered saline.
Lenses made from Formulation II Containing Silver Nano-Particles A polymerizable dispersion is prepared by adding silver nitrate in a volume of formulation II to have $AgNO_3$ concentration equal to 500 ppm. Silver nitrate is dissolved easily in formulation II under stirring. An amount of the dispersion is introduced into each polypropylene molds and cured for 60 minutes under UV light to form contact lenses. The lenses are then extracted in isopropyl alcohol. (IPA), then packaged and autoclaved in phosphate buffered saline.

When examining obtained lenses under dark field microscope, silver nano-particles are found to be distributed uniformly within the lenses.

Lenses made from Formulation II with Silver Powder in the Formulation.

A polymerizable mixture is prepared by adding nanosize activated silver powder (99.9+% Ag, from Aldrich) in an amount of formulation II to have the concentration of nanosize activated silver powder equal to about 500 ppm. The nanosize activated silver powder does not dissolve in the formulation, and therefore by sonication large particles are forced to be dispersed in the formulation, which caused the change of transparent blue formulation into cloudy blue formulation. An amount of the mixture is introduced into each polypropylene molds and cured for 60 minutes under UV light to form contact lenses. The lenses are then extracted in isopropyl alcohol (IPA), then packaged and autoclaved in phosphate buffered saline.

Under dark field microscope, whitish particles are observed and the distribution of the particles is not uniform comparing with other lenses prepared in this example.

EXAMPLE 15

Contact Lenses Containing Ag NP and Different Concentration of Stabilizer.

A polymerizable dispersion is prepared by adding calculated amount of silver stock solution (SSS) into a calculated amount of formulation I. The silver stock solution is prepared by adding calculated amount of polyacrylic acid (PAA) and silver salt (such as silver nitrate) into a given amount of dimethylacrylamide (DMA). The mixture of formulation I with silver stock solution is stirred for 4 hr or longer at room temperature to form silver nano-particles before making contact lenses by means of molding in polypropylene molds. An amount of the polymerizable dispersion with silver nano-particles is introduced into each polypropylene molds and cured for 30 minutes under UV light to form contact lenses. The lenses are then extracted in isopropyl alcohol (IPA), then packaged and autoclaved in phosphate buffered saline.

The silver-nano particle formation is controlled by the relative concentration of silver to PAA, as indicated by the color change of the formulation. For formulations with either 300 ppm or 500 ppm of silver nitrate, when the molar ratio of $AgNO_3$/PAA (note that the molar ratio is calculated based on the molecular weight of silver nitrate and the molecular weight of the repeating unit of PAA) changes from 4/1, 2/1, 1/1, 1/2, 1/4, to 1/8, the color of the formulation changes from obvious yellow, to less obvious yellow, and to even almost no color. Since yellow is the characteristic color of silver nano-particles, this phenomena indicates that the formation of the PAA-stabilized silver nano-particles can be controlled by the relative concentration of silver to PAA.

The in-vitro activity of the formed contact lenses are assayed against S. aureus.#6538 according the procedures described in example 11. It is discovered that the activity is controlled by silver concentration and the relative concentration of silver to PAA. For lenses made from formulations with either 300 ppm or 500 ppm of silver nitrate, the lenses may or may not show in-vitro antimicrobial activity, characterized by about 99% to almost 0% inhibition of viable cells as compared to the control lenses, depending on the molar ratio of $AgNO_3$/PAA (note that the molar ratio is calculated based on the molecular weight of silver nitrate and the molecular weight of the repeating unit of PAA). Ag/PAA ratio from 4/1 to 1/4 is preferred, and more preferably from 1/2 to 2/1 is preferred. Ag/PAA of 1/8 is generally not preferred. Similar results are found for blue formulation I (formulation I which contains copper phthalocyanine blue pigments).

It is understood that the molecular weight of PAA used here is about 2000. PAA with molecular weight higher or lower than 2000 can also be used. Although the sodium salt of PAA (PAANa) is not preferred.

EXAMPLE 16

Visibility-Tinted Contact Lenses Containing PAA Stabilized Ag NP and Different Colorants A contact lens prepared from formulation I with AgNP or PAA stabilized AgNP may appears to be yellowish. A color adjuster (e.g. a pigment or a dye, such as copper phthalocyanine (CuP blue), and/or carbazole violet (CV), phthalocyanine green (PCN green), or reactive blue dyes (e.g., blue HEMA)) is used to impart the lenses with desired color appearance and handling tint. CuP blue or PCN green pigment is dispersed in TRIS. Polymerizable dispersions are prepared by adding calculated amount of silver stock solution (SSS) into a calculated amount of formulation I contains certain concentration of color adjuster. The silver stock solution is prepared by adding calculated amount of polyacrylic acid (PAA) and silver salt (such as silver nitrate) into a given amount of dimethylacrylamide (DMA). The mixture of formulation I with silver stock solution is stirred for 4 hr or longer at room temperature to form silver nano-particles. The formulations are then stored at 4° C. until being degassed to remove oxygen and then ready for making contact lenses by means of molding in polypropylene molds. An amount of the polymerizable dispersion with silver nano-particles is introduced into each polypropylene molds and cured for 30 minutes under UV light to form contact lenses. The lenses are then extracted in isopropyl alcohol (IPA), then packaged and autoclaved in phosphate buffered saline.

The in-vitro activity of the formed contact lenses are assayed against Pseudomonas aeruginosa GSU #3 according the procedures described in example 11. As shown in Table 6, the color adjusters impart the contact lens with handling color tint and do not appear to adversely affect the in-vitro activity against Pseudomonas aeruginosa.

TABLE 6

| Colorant and concentration | [$AgNO_3$] ppm | [PAA] ppm | % of Inhibition |
|---|---|---|---|
| CuP, 60 ppm | 500 | 212 | >99% |
| CuP, 90 ppm | 456 | 212 | >99% |
| CuP, 90 ppm | 200 | 93 | >99% |
| CuP, 120 ppm | 456 | 212 | >99% |
| CuP, 120 ppm | 200 | 93 | >99% |
| CuP, 60 ppm, CV, 8 ppm | 456 | 212 | >99% |
| PCN, 60 ppm | 456 | 212 | >99% |
| PCN, 60 ppm | 200 | 93 | >99% |

Colorants (such as CuP and PCN) may also be modified by amphiphilic copolymers (e.g. poly(ethyl acrylate)-polyacrylic acid (PEA-PAA) copolymer)

EXAMPLE 17

Different Stabilizers for Silver Stock Solution Preparation

To prepare a formulation containing AgNP, one of the approaches is to prepare a silver stock solution (SSS) and then mix the SSS with the formulation. Generally there is no AgNP formation in SSS, or only a percentage of Ag+ is converted to AgNP in SSS. All or majority of AgNP forms in-situ when mixing SSS with formulation. In addition to PAA as a stabilizer for silver stock solution preparation, other stabilizers are also studied. Both small molecules and polymers are studied.

Small molecules that can function as stabilizer in silver stock solution preparation includes acrylic acid, citric acid, etc. For polymers, both charged and non-charger polymers and amphiphilic polymers are studied. Some of the examples of stabilizers include PAA and polyvinylpyrrolidone (PVP) of different molecular weights. The sodium salt of PAA (PAANa) is also tried to be used as a stabilizer in silver stock solution preparation. Other polymers, including polyethylene glycol (PEG), polyethylene imine (PEI), polydimethylsiloxane-polyacrylic acid (PDMS-PAA) copolymer, poly(ethyl acrylate)-polyacrylic acid (PEA-PAA) copolymer, are also studied and they appears to be not as good as compared to PAA.

EXAMPLE 18

"Step-by-Step" Preparation of Formulation Containing AgNP

As disclosed in example 17, to prepare a formulation containing AgNP, one of the approaches is to prepare a silver stock solution (SSS) and then mix the SSS with the formulation. Instead of mixing SSS with formulation which consists of macromer, TRIS, DMA, Darocure and ethanol as shown in example 1, another approach is to mix SSS with formulation components. Since the formulation consists of multiple components, there are multiple possibilities in which SSS can be mixed in. However, the order of mixing SSS, or in other words, to mix SSS with which component first, is very important to form a formulation with stable AgNP suspension. As an example, the SSS is mixed with TRIS first, then the mixture of Tris and SSS is immediately (within about 1 min) added into macromer. The mixture of macromer and TRIS/SSS is stirred for about 20 min. Then DMA is added into the mixture and stirred for 20 min, followed by ethanol. The mixture is then stirred for 60 min before Darocure is added. The final mixture is stirred for another 90 min. The formulation prepared in this way contains AgNP as indicated by the characteristic UV absorption peak around 400 nm.

EXAMPLE 19

Preparation of Formulation Containing AgNP using Stabilized AgNP-ethanol Solution Another approach to prepare a formulation containing AgNP is to use stabilized AgNP-ethanol solution. After studying different stabilizers which are capable of forming stabilized AgNP in ethanol, polyvinylpyrrolidone (PVP) is chosen as the stabilizer in this approach. PVP-stabilized AgNP solution in ethanol is prepared by dissolving calculated amount of PVP in ethanol, followed by adding desired amount of silver salt (e.g. silver nitrate). The AgNP is then produced by using a reducing agent, such as sodium borohydride ($NaBH_4$). The PVP-stabilized AgNP-ethanol solution is very stable over time, based on the constant UV adsorption peak around 400 nm monitored over a week. This PVP-stabilized AgNP-ethanol solution is then mixed with the other components (macromer, Tris, DMA and Darocure) to form a formulation containing AgNP. Depending on the preparation conditions (e.g., silver concentration, PVP molecular weight, and PVP:Ag ratio, etc), some particles may form when mixing PVP-stabilized AgNP-ethanol solution into the formulation components. Those obvious particles formed during the process can be easily removed by filtration.

As an example, a PVP-stabilized AgNP-ethanol is prepared by dissolving 0.0588 gram of PVP (Mw of 55000) into 300 gram of ethanol. After 20 min of stirring, 0.06 gram of silver nitrate solid as added. After another 20 min stirring, a calculated amount of $NaBH_4$ aqueous solution is added into the mixture, to achieve a molar ratio of 1.5:1:1 for PVP: $AgNO_3$:$NaBH_4$. A stirring of at least 20 min is allowed. The final solution is clear with a golden color due to the presence of PVP-stabilized AgNP, which is also confirmed by a characteristic UV absorption peak around 400 nm. It is obvious to those who are skill in the art that PVP of other molecular weights and different PVP:Ag ratios can be used A formulation I with 60 ppm of CuP, 50 ppm of $AgNO_3$ and 49 ppm of PVP is then prepared by mixing appropriate amount of macromer, Tris-CuP, DMA, Darocure and PVP-stabilized AgNP-ethanol solution. The formulation is filtered to remove any particles which are bigger than 5 microns and degassed for casting lenses. The in-vitro activity of the formed contact lenses are assayed against *Pseudomonas aeruginosa* GSU #3 according to the procedures described in example 11. The lenses with PVP-stabilized silver nanoparticles show antimicrobial activity, characterized by 98% inhibition of viable cells as compared to the control lenses.

EXAMPLE 20

Prolong In-vitro Antimicrobial Activity of AgNP-Containing Contact Lenses

The prolong in-vitro antimicrobial activities of Ag nanoparticle-containing contact lenses are studied by testing their in-vitro antimicrobial activities against *Pseudomonas aeruginosa* GSU #3 and *Staphylococcus aureus* ATCC #6538 after at least 5 consecutive soaking/rinsing cycles, each cycle comprising soaking/rinsing each lens in a phosphate buffered saline (PBS) or ClearCare® (CIBA Vision) for a period of time from about 24 to about 72 hours. After a desired numbers of consecutive soaking/rinsing cycles, each lens is challenged with viable microorganisms and in-vitro antimicrobial activities are tested according to the method described in Example 11.

It is understood that in studies of the prolong in-vitro antimicrobial activities of Ag nanoparticle-containing contact lenses, any appropriate test solution can be used in soaking/rinsing lenses.

Phosphate Buffered Saline

Studies of the prolong in-vitro antimicrobial activities of Ag nanoparticle-containing contact lenses are performed in sterile glass or plastic (10 mL) lens vials as follows. One lens is placed in each vial and about 2.0 mL of PBS is aseptically delivered to the vial. Care is taken to ensure that the lens is submerged within PBS. Soaking/rinsing solution (PBS) is exchanged almost daily. However, solution exchanges are not performed on weekends or holidays. In such instances solution exchange occurs on the next work day. The vial is capped and left at ambient temperature until the next work day. After about 24-72 hours the old soaking/rinsing solution is decanted and about 2.0 mL of fresh soaking/rinsing solution is aseptically delivered to the vial as described above. In most studies 30 cycles are conducted over a 6 week period (no cycling is performed on weekends or holidays). After 30 consecutive soaking/rinsing cycles in PBS, lenses are subsequently challenged with *P. aeruginosa* GSU#3 and *S. aureus* 6538 respectively. The results are reported in Table 8.

ClearCare® Solution

ClearCare® solution (CIBA Vision) is one-bottle, no-rub, no-rinse hydrogen peroxide-based lens care solution for soft contact lenses. Studies of the prolong in-vitro antimicrobial activities of Ag nanoparticle-containing contact lenses are performed by testing their in-vitro antimicrobial activities against *Pseudomonas aeruginosa* GSU #3 and *Staphylococcus aureus* ATCC #6538 after at least 5 consecutive soaking/ rinsing cycles, each cycle comprising soaking/rinsing each lens in ClearCare® solution. Soaking/rinsing of lenses is performed in the AOcup (lens care case provided with Clear-Care®) and having disc-on-stem configuration) with a platinum neutralizer disc. One lens is placed in each of the right and left lens baskets. ClearCare® solution is manually squirted into the case up to the fill line (approx 10-11 mL). Soaking/rinsing solution (ClearCare®) is exchanged almost daily. However, solution exchanges are not performed on weekends or holidays. In such instances solution exchange occurs on the next work day. The case cap is closed and finger-tightened and the filled cases left at ambient temperature until the next day. After about 24-72 hours the old soaking/rinsing solution is decanted and the case filled once again with fresh ClearCare® as described above. In most studies 30 cycles are conducted over a 6 week period (no cycling is performed on weekends or holidays). After 5 consecutive soaking/rinsing cycles in ClearCare® lens disinfecting solution, lenses are subsequently challenged with $P.$ $aeruginosa$ GSU#3 and $S.$ $aureus$ 6538 respectively and the results are reported in Table 7. After 30 consecutive soaking/rinsing cycles in ClearCare® lens disinfecting solution, lenses are subsequently challenged with $P.$ $aeruginosa$ GSU#3 and $S.$ $aureus$ 6538 respectively and results are reported in Table 8.

TABLE 7

| LENS | Pecentage of inhibition of viable cells as compared to control lenses* | | | | | |
|---|---|---|---|---|---|---|
| | 0 CYCLE | | 5 CYCLEs in PBS | | 5 cycles in ClearCare ® | |
| TYPE | P. aeruginosa | S. aureus | P. aeruginosa | S. aureus | P. aeruginosa | S. aureus |
| SPB3.0# | >99.9 | 98.7 | ND | ND | 97.5 | 99.7 |

*Control lenses are Lotrafilcon A (CIBA Vision) lenses. Number of surviving organisms (cfu) recovered from CONTROL lenses @ 24 hours assay contact time are 2110 cfu for $P.$ $aeruginosa$ and 7073 cfu for $S.$ $aureus.$
Visibility-tinted contact lenses, prepared according to the procedure described in Example 16 ([AgNO$_3$] 500 ppm, [PAA] = 212 ppm and [Cup] = 60 ppm), contains PAA stabilized Ag NP.

TABLE 8

| LENS | Pecentage of inhibition of viable cells as compared to control lenses* | | | | | |
|---|---|---|---|---|---|---|
| | 0 CYCLE | | 30 Cycles in PBS | | 30 Cycles in ClearCare ® | |
| TYPE | P. aeruginosa | S. aureus | P. aeruginosa | S. aureus | P. aeruginosa | S. aureus |
| SPB3.0[1] | 99.8 | 93.5 | 99.9 | 91.3 | 92.6** | 93.1 |
| SPB3.x[2] | 99.9 | 98.6 | 99.9 | 91.9 | ND | 98.9 |

*Control lenses are Lotrafilcon A (CIBA Vision) lenses. Number of surviving organisms (cfu) recovered from CONTROL lenses @ 24 hours assay contact time are 34500 cfu for $P.$ $aeruginosa$ and 21167 cfu for $S.$ $aureus.$
**Significant loss of antimicrobial activity after 30 soaking/rinsing cycles in ClearCare (>1.5 log reduction of viable microorganisms) as compared to PBS cycled, however the lenses still posses significant antimicrobial activity as compared to control lenses.
[1]Visibility-tinted contact lenses, prepared according to the procedure described in Example 16 ([AgNO$_3$] = 500 ppm, [PAA] = 212 ppm and [Cup] = 60 ppm), contains PAA stabilized Ag NP.
[2]Visibility-tinted contact lenses, prepared according to the procedure described in Example 16 ([AgNO$_3$] = 200 ppm, [PAA] = 85 ppm and [Cup] = 60 ppm), contains PAA stabilized Ag NP.

Table 8 shows that there is no apparent change in microbicidal activity against $Staph.$ $Aureus$ or against $Pseudomonas$ challenge organism even after 30 consecutive soaking/rinsing cycles in PBS (after direct contact with PBS over a period of six weeks).

Table 7 shows that there is no apparent change in microbicidal activity against $Staph.$ $Aureus$ or against $Pseudomonas$ challenge organism even after 5 consecutive soaking/rinsing cycles in ClearCare® (after direct contact with PBS over a period of about 5 to 7 days). No apparent change is observed in microbicidal activity against $Staph.$ $aureus.$ There is a significant reduction in microbicidal activity against $Pseudomonas$ $aeruginosa$ after 30 consecutive soaking/rinsing cycles in ClearCare® (after direct contact with ClearCare® over a period of six weeks).

EXAMPLE 21

Silver Analysis of Lenses and Package Saline

The silver concentrations in lenses and in saline are measured by graphite furnace atomic absorption (GFAA) or Instrumental Neutron Activation Analysis (INAA). In typical GFAA, silver in lenses is digested by 40% acidified magnesium solution and digested solution is analyzed by GFM for silver concentration. In typical INM, stable nuclides ($^A Z$) in the sample undergo neutron capture reactions in a flux of neutrons. The radioactive nuclides ($^{A+1}Z$) produced in this activation process will, in most cases, decay through the emission of a beta particle ($\beta^-$) and gamma ray(s) with a unique half-life. A high-resolution gamma-ray spectrometer is used to detect these "delayed" gamma rays from the artificially induced radioactivity in the sample for both qualitative and quantitative analysis. When a sample that contains silver is irradiated, a fraction of the $^{109}$Ag atoms in the sample will capture a neutron and become $^{110}$Ag. The $^{110}$Ag atoms are radio active and have a half-life of 24.6 seconds. When the $^{110}$Ag atoms beta decay to $^{110}$Cd, a 658 keV gamma ray is emitted 4.5% of the time. The amount of silver in the original sample can be determined by measuring the number of 658 keV gamma-rays emitted from the sample in a given time interval after the sample has been exposed to a flux of neutrons.

Contact lenses are removed from saline, rinsed with deionized H2O, and air dried overnight. Dried contacts are weighed and sealed in baggy. Saline from individual lens package is mixed and then transferred to a tarred vial and weighed. Samples are analyzed in sequence, under identical irradiation, decay, and counting conditions. Known Ag standards are inserted at a ratio of about 10:1. Fluorine is present in these contact lenses. Irradiation condition may be altered to reduce the background caused by high F if lower Ag detection limits are desired. Spectra are analyzed by determining peak and background areas and applying a calibration factor derived from the standards used.

A batch of lenses is prepared from a formulation I containing 50 ppm of $AgNO_3$. Two of the lenses are analyzed by INM. The silver concentrations in lenses are 30.0±2.43 ppm and 29.0±2.35 ppm. The silver concentration in saline is 0.13±0.02 ppm.

A batch of lenses is prepared from a formulation I containing 500 ppm of $AgNO_3$. Two of the lenses are analyzed by INM. The silver concentrations in lenses are 65.0±4.16 ppm and 51.0±3.47 ppm. Partial precipitation of silver nano-particles from this formulation containing no stabilizer may be attributed to the low silver concentration of lenses in this experiment. The silver concentration in saline is 0.34±0.03 ppm.

A batch of lenses is prepared from a formulation I containing 300 ppm of $AgNO_3$ and 127 ppm of PAA and 60 ppm of copper phthalocyanine blue (PCN blue, also referred to as CuP). The silver concentrations of lenses at different process steps are analyzed by INM. The data is presented in Table 9. Some silver from the lenses is eluted to IPA during extraction and to saline during storage.

TABLE 9

| Samples | Silver concentration (ppm) |
| --- | --- |
| Three lens, not extracted | 127.0 ± 7.112, 122.0 ± 6.832, 113.0 ± 6.441 |
| Three dry Lens, plasma coated | 119.0 ± 6.664, 120.0 ± 6.720, 131.0 ± 7.336 |
| Three plasma coated lenses, autoclaved in saline | 62.1 ± 3.974, 69.4 ± 4.233, 74.5 ± 4.470 |
| Combined saline from three lenses | 0.389 ± 0.029 |
| IPA used in the extraction | 0.019 ± 0.009 |

Four batches of lenses are prepared from a formulation I containing 500 ppm of $AgNO_3$ and 60 ppm of CuP, and different concentration of PAA (from 53 ppm to 424 ppm). The silver concentrations in lenses and in saline are measured by INM and listed in table 10.

TABLE 10

| Formulation | Sample | Average silver concentration (ppm)* |
| --- | --- | --- |
| Formulation I, with 500 ppm of $AgNO_3$, 60 ppm of CuP, and 53 ppm of PAA | Lens saline | 81.4 ± 12.40 0.40 ± 0.028 |
| Formulation I, with 500 ppm of $AgNO_3$, 60 ppm of CuP, and 106 ppm of PAA | Lens saline | 97.4 ± 29.34 0.60 ± 0.039 |
| Formulation I, with 500 ppm of $AgNO_3$, 60 ppm of CuP, and 212 ppm of PAA | Lens saline | 75.13 ± 5.21 0.30 ± 0.023 |
| Formulation I, with 500 ppm of $AgNO_3$, 60 ppm of CuP, and 424 ppm of PAA | Lens saline | 66.7 ± 31.53 0.40 ± 0.029 |

*Average silver concentration from 3 lenses or combined saline

A batch of lenses is prepared from a formulation I containing 300 ppm of $AgNO_3$ and 127 ppm of acrylic acid (AA) and 60 ppm of CuP. Two of the lenses are analyzed by INAA. The silver concentrations in lenses are 235.0±12.69 ppm and 210.0±11.55 ppm. The silver concentration in saline is 0.43±0.036 ppm.

Two batches of lenses are prepared from a formulation I containing 120 ppm of CuP and different concentration of 500 ppm of $AgNO_3$ (from 200 to 456) and PAA (from 93 ppm to 212 ppm). The silver concentrations in lenses and in saline are measured by INAA and listed in table 11.

TABLE 11

| Formulation | Sample | Average silver concentration (ppm)* |
| --- | --- | --- |
| Formulation I, with 200 ppm of $AgNO_3$, 120 ppm of CuP, and 93 ppm of PAA | Lens saline | 82.0 ± 4.95 0.40 ± 0.029 |
| Formulation I, with 456 ppm of $AgNO_3$, 120 ppm of CuP, and 212 ppm of PAA | Lens saline | 86.0 ± 5.10 0.40 ± 0.030 |

*Average silver concentration from 3 lenses or combined saline

Three batch of lenses are prepared from formulation I containing different pigments, such as copper phthalocyanine blue (CuP), copper phthalocyanine green (PCNG), and/or carbazole violet (CV) The silver concentrations in lenses and in saline are measured by INM and listed in table 12.

TABLE 12

| Formulation | Sample | Average silver concentration (ppm)* |
| --- | --- | --- |
| Formulation I, with 456 ppm of $AgNO_3$, 60 ppm of PCNG, and 212 ppm of PAA | Lens saline | 108.6 ± 6.38 0.40 ± 0.031 |
| Formulation I, with 200 ppm of $AgNO_3$, 60 ppm of PCNG, and 93 ppm of PAA | Lens saline | 112.0 ± 6.46 0.30 ± 0.027 |
| Formulation I, with 456 ppm of $AgNO_3$, 60 ppm of CuP, 8 ppm of CV, and 212 ppm of PAA | Lens saline | 87.3 ± 5.33 0.40 ± 0.030 |

*Average silver concentration from 3 lenses or combined saline

The silver concentration of some of the lenses is also analyzed by GFM. Table 13 listed the silver concentration of some lenses and their package saline.

TABLE 13

| Formulation | Sample | Average silver concentration (ppm) |
| --- | --- | --- |
| Formulation I, with 456 ppm of $AgNO_3$, 60 ppm of PCNG, and 212 ppm of PAA | Lens saline | 207.3 ± 0.1 0.566 ± 0.0006 |
| Formulation I, with 200 ppm of $AgNO_3$, 60 ppm of PCNG, and 93 ppm of PAA | Lens saline | 132.3 ± 0.1 0.355 ± 0.0006 |
| Formulation I, with 456 ppm of $AgNO_3$, 60 ppm of CuP, 8 ppm of CV, and 212 ppm of PAA | Lens saline | 97.5 ± 0.1 0.478 ± 0.0006 |
| Formulation I, with 500 ppm of $AgNO_3$, and 106 ppm of PAA | Lens saline | 53.9 ± 0.1 0.507 ± 0.0006 |
| Formulation I, with 500 ppm of $AgNO_3$, and 106 ppm of PAA | Lens saline | 44.4 ± 0.1 0.470 ± 0.006 |

EXAMPLE 22

Effect of Lens Care Solution on the Silver Concentration in Lenses.

A batch of lenses is made from a formulation I containing 500 ppm of $AgNO_3$ and 60 ppm of CuP and 212 ppm of PAA. Three lenses are stored in original package in saline as control (A1 to A-3, Table 14). 4 groups of three lenses each (A-4 to A15, Table 14) are underwent 30 consecutive soaking/rinsing ccyles in different liquid media (e.g. PBS saline) or lens care solutions (SoloCare®, ClearCare®), both from CIBA Vision,) according to procedure described in Example 20 or lens care procedures specified for the product by the manufacturer. After 30 soaking/rinsing cycles, all lenses are analyzed by INM for silver concentration. As indicated in Table 14, ClearCare® has the most impact to the silver concentration, with about 90% loss of silver from the lens after 30 soaking/rinsing cycles. Soaking/rinsing with SoloCare® (5 minutes and 6 hours cycling regimens) cause approximately 50% loss of silver from the lens after 30 cycles.

TABLE 14

| Sample ID | Mass | Silver (wt %) |
|---|---|---|
| A-1 | 0.0154 g | 46.5 ppm (±3.534 ppm) |
| A-2 | 0.0157 g | 46.0 ppm (±3.450 ppm) |
| A-3 | 0.0161 g | 50.6 ppm (±3.593 ppm) |
| Saline | 1.382 g | 0.5 ppm (±0.037 ppm) |
| A-4(5 min SoloCare ®) | 0.0165 g | 21.1 ppm (±2.700 ppm) |
| A-5(5 min SoloCare ®) | 0.0161 g | 18.4 ppm (±2.359 ppm) |
| A-6(5 min SoloCare ®) | 0.0165 g | 20.3 ppm (±2.416 ppm) |
| Saline | 1.369 g | 0.1 ppm (±0.035 ppm) |
| A-7(6 hr SoloCare ®) | 0.0164 g | 24.9 ppm (±2.639 ppm) |
| A-A-8(6 hr SoloCare ®) | 0.0162 g | 22.2 ppm (±2.531 ppm) |
| A-9(6 hr SoloCare ®) | 0.0157 g | 21.1 ppm (±2.659 ppm) |
| Saline | 1.376 g | 0.1 ppm (±0.033 ppm) |
| A-10 (ClearCare ®) | 0.0160 g | 4.5 ppm (±2.650 ppm) |
| A-11 (ClearCare ®) | 0.0157 g | <4.0 ppm |
| A-12 (ClearCare ®) | 0.0154 g | <4.0 ppm |
| Saline | 1.408 g | <0.04 ppm |
| A-13 (PBS) | 0.0158 g | 14.6 ppm (±2.292 ppm) |
| A-14 (PBS) | 0.0156 g | 10.6 ppm (±2.025 ppm) |
| A-15 (PBS) | 0.0152 g | 23.6 ppm (±2.478 ppm) |
| Saline | 1.426 g | <0.04 ppm |

EXAMPLE 23

The silver concentration of 5 samples (formulation I with or without $AgNO_3$) are analyzed by INAA and listed in Table 15.

TABLE 15

| Formulation | Theoretical [Ag] (PPm) | Measured [Ag] (ppm) |
|---|---|---|
| Formulation I, | 0 | <1.0 |
| Formulation I, with 500 ppm of $AgNO_3$, 60 ppm of CuP, and 212 ppm of AA | 317.6 | 286.0 ± 14.58 |
| Formulation I, with 200 ppm of $AgNO_3$, 60 ppm of CuP, and 84.8 ppm of AA | 127.1 | 117 ± 6.08 |
| Formulation I, with 500 ppm of $AgNO_3$, 60 ppm of CuP, and 212 ppm of PAA | 317.6 | 282.0 ± 14.38 |
| Formulation I, with 200 ppm of $AgNO_3$, 60 ppm of CuP, and 84.8 ppm of PAA | 127.1 | 110 ± 5.720 |

Five batches of lenses are prepared from a lens-forming material (formulation I containing 500 ppm of $AgNO_3$, 60 ppm of CuP, and 212 ppm of PAA) and each stored in saline in a package. The silver concentrations in lenses and in saline are measured by INM and listed in Table 16. It appears that the silver concentrations in lenses can be affected to a certain degree by process conditions, for example, by the staging time (days after the lenses are cured until they are further processed by IPA extraction). The silver concentrations in saline for these five batches of lenses are in the range of from 0.30 to 0.45 ppm.

TABLE 16

| Lens batch #1 | Staging time (days) | Average silver concentration (ppm)* |
|---|---|---|
| #1 | 5 | 62.2 ± 3.76 (in lens) |
| | | 0.35 ± 0.033 (in saline) |
| #2 | 46 | 160.3 ± 8.91 (in lens) |
| | | 0.45 ± 0.034 (in saline) |
| #3 | 46 | 160.0 ± 8.90 (in lens) |
| | | 0.34 ± 0.030 (in saline) |

TABLE 16-continued

| Lens batch #1 | Staging time (days) | Average silver concentration (ppm)* |
|---|---|---|
| #4 | 5 | 44.8.0 ± 3.42 (in lens) |
| | | 0.44 ± 0.034 (in saline) |
| #5 | 5 | 75.4 ± 8.90 (in lens) |
| | | 0.41 ± 0.034 (in saline) |

*Average silver concentration from 3 lenses or combined saline

EXAMPLE 24

Contact lenses (referred to as test lenses) made from a formulation in Example 16 (which contains 60 ppm of CuP and 500 ppm of $AgNO_3$ in the formulation) are evaluate on eyes. A double-masked, contralateral study is conducted. The test lenses and Focus Night & Day (FND) control lenses are randomly assigned to either eye in all subjects. The duration of wear is 26 hours, including eight hours of eye closure (sleep). The clinical results indicates that both the test and control lenses behaved similarly during this study. No significant difference is observed in lens surface characteristics when comparing the test lenses and the FND control lenses. The silver particles are distinguishable under bio-microscope but not to the naked eyes. The level of silver used in the test lenses is safe for overnight wear as there are no observable, adverse ocular effects resulted from their wear.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for making an antimicrobial medical device, comprising the steps of: obtaining a polymerizable fluid composition comprising a siloxane-containing macromer and a vinylic monomer capable of reducing silver cations; adding a desired amount of a soluble silver salt into the fluid composition to form a polymerizable dispersion comprising silver nanoparticles and said silver nanoparticles having a stability of at least about 60 minutes, wherein the silver nanoparticles are formed by reducing the silver cations in the soluble silver salt with the vinylic monomer; introducing an amount of the polymerizable dispersion in a mold for making a medical device; and polymerizing the polymerizable dispersion in the mold to form the antimicrobial medical device containing silver nanoparticles.

2. The method of claim 1, wherein the medical device is an ophthalmic device.

3. The method of claim 2, wherein the polymerizable fluid composition is selected from the group consisting of formulations of lotrafilcon A, lotrafilcon B, etafilcon A, genfilcon A, lenefilcon A, polymacon, acquafilcon A, and balafilcon.

4. The method of claim 2, wherein the siloxane-containing macromer is selected from the group consisting of Macromer A, Macromer B, Macromer C, and Macromer D, wherein Macromer A is a polysiloxane macromer having a number-average molecular weight of 2000 to 10,000 and the the segment of the formula:

CP—PAO-DU-ALK—PDMS-ALK-DU-PAO—CP where PDMS is a divalent poly(disubstituted siloxane), ALK is an alkylene or alkylenoxy group having at least 3 carbon atoms, DU is a diurethane-containing group, PAO is a divalent polyoxyalkylene, and CP is selected from acrylates and methacrylates, wherein Macromer B is a polysiloxane-comprising perfluoroalkyl ether and has the formula:

$P_1$—(Y)$_m$-(L-X$_1$)p-Q-(X$_1$-L)$_p$-(Y)$_m$—$P_1$ where each $P_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each $X_1$, independently of the others, is —NHCO—, —CONH—, —NH-CONH—, —COO—, —OCO—, —NHCOO— or —OCONH—; and Q is a bivalent polymer fragment consisting of the segments:

(a) -(E)$_k$-Z—CF$_2$—(OCF$_2$)$_x$—(OCF$_2$CF$_2$)$_y$—OCF$_2$—Z-(E)$_k$-, where x+y is a number in the range of from 10 to 30; each Z, independently of the others, is a divalent radical having up to 12 carbon atoms or Z is a bond;

each E, independently of the others, is —(OCH$_2$CH$_2$)$_q$—, where q has a value of from 0 to 2, and where the link —Z-E- represents the sequence —Z—(OCH$_2$CH$_2$)$_q$—; and k is 0 or 1;

(b)

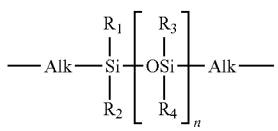

wherein is an integer from 5 to 100; Alk is alkylene having up to 20 carbon atoms; 80-100% of the radicals $R_1$, $R_2$, $R_3$ and $R_4$, independently of one another, are alkyl and 0-20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NH-COO— or OCONH—;

with the provisos that there must be at least one of each segment (a), (b), and (c) in Q, that each segment (a) or (b) has a segment (c) attached to it, and that each segment (c) has a segment (a) or (b) attached to it;

wherein Macromer C has an average molecular weight of from about 300 to about 30,000 and comprises at least one segment of the formula (I), (IV), (V), (VI) or (VII):

—a—Z—b—     (I)
     |
     d

—a—X$_1$—b—     (IV)
     |
     d a—(X$_1$—b)$_q$     (V)
   |
  (d)$_x$

—(a—X$_1$—b)$_q$—     (VI)
     |
   (d)$_x$ (d)$_x$     (d)$_x$     (VII)
 |        |
b—X$_1$—a—X$_1$—b
 |        |
(d)$_x$     (d)$_x$ in which (a) is a polysiloxane segment; (b) is a polyol segment which contains at least 4 carbon atoms; Z is a segment (c) or a group $X_1$; (c) is defined as $X_2$—R—$X_2$, wherein R is a bivalent radical of an organic compound having up to 20 carbon atoms and each $X_2$ independently of the other is a bivalent radical which contains at least one carbonyl group; $X_1$ is defined as $X_2$; x is 0, 1 or 2; q has an average numerical value of 1-20; and (d) is a radical of the formula (II):

$X_3$-L-(Y)$_k$—$P_1$     (II)

in which $P_1$ is alkenyl, alkenylaryl or alkenylarylenealkyl having up to 20 carbon atoms;

Y and $X_3$ independently of one another are a bivalent radical which contains at least one carbonyl group; k is 0 or 1; and L is a bond or a divalent radical having up to 20 carbon atoms of an organic compound, wherein the polysiloxane segment (a) is derived from a compound of the formula (III):

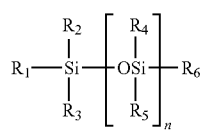

in which n is an integer from 5 to 500; 99.8-25% of the radicals $R_1$, $R_2$, $R_3$, $R_4$, $R_5$ and $R_6$ independently of one another are alkyl and 0.2-75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-NH$_2$ or alk-(OCH$_2$)$_m$—(OCH$_2$)p-OR$_7$, $R_7$ is hydrogen or lower alkyl, alk is alkylene, and m and p independently of one another are an integer from 0 to 10, one molecule containing at least one primary amino or hydroxyl group, wherein the alkylenoxy groups —(OCH$_2$CH$_2$)$_m$ and —(OCH$_2$)$_p$ in formula (III) are either distributed randomly in a ligand alk-(OCH$_2$CH$_2$)$_m$—(OCH$_2$)$_p$-OR$_7$ or are distributed as blocks in a chain, wherein the polysiloxane segment (a) in formula (I) is linked a total of 1-50 times, via a group Z with the segment (b) or another segment (a), Z in an a-Z-a sequence always being a segment (c), wherein the segments (b) in Macromer C according to the formula (VI) are linked in total (per molecule) with up to 20 with up to 6 polymerizable segments (d), wherein the average number of segments (d) per molecule of the formula (VII) is in the range from 2 to 5, and very preferably is in the range from 3 to 4, wherein macromer D has the formula:

ACRYLATE-LINK-ALK-O-ALK-PDAS-ALK-O-ALK-LINK-ACRYLATE in which the ACRYLATE is selected from acrylates and methacrylates; LINK is selected from urethanes and dirurethane linkages; ALK-O-ALK is $R_1$—O—$R_2$ or $R_3$—O—$R_4$, $R_1$, $R_2$, $R_3$, and $R_4$, independently of one another, are lower alkylene; and PDAS is a poly(dialkylsiloxane) having a segment of the formula:

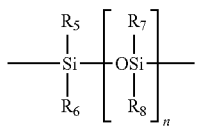

in which n is an integer from about 5 to about 500; and $R_5$, $R_6$, $R_7$, and $R_8$ are, independently of one another, are lower alkyl.

5. The method of claim 1, wherein the polymerizable fluid composition comprises a siloxane-containing monomer and/or a hydrophilic vinylic monomer.

6. The method of claim 5, wherein the polymerizable fluid composition comprises: (a) about 20 to 40 weight percent of a siloxane-containing macromer, (b) about 5 to 30 weight percent of a siloxane-containing monomer, and (c) about 10 to 35 weight percent of a hydrophilic vinylic monomer.

7. The method of claim 1, wherein the vinylic monomer capable of reducing silver cations is selected from the group consisting of acrylamide, methacrylamide, di(lower alkyl)acrylamides, di(lower alkyl)methacrylamides, (lower allyl)acrylamides, (lower allyl)methacrylamides, hydroxyl-substituted (lower alkyl)acrylamides, hydroxyl-substituted (lower alkyl)methacrylamides, and N-vinyl lactams.

8. The method of claim 7, wherein the vinylic monomer is N,N-dimethylacrylamide (DMA) or N-vinyl-2-pyrrolidone (NVP).

9. The method of claim 1, wherein the polymerizable fluid composition further comprises a biocompatible reducing agent.

10. The method of claim 1, wherein the polymerizable fluid composition further comprises a stabilizer for stabilizing silver nano-particles.

11. The method of claim 10, wherein the stabilizer is a polyacrylic acid (PAA), a poly(ethyleneimine) (PEI), a poly(vinylpyrrolidone) (PVP), a copolymer of acrylic acid (AA) with a vinylic monomer, acrylic acid, or polyionic material having carboxyl, amino and/or sulfur-containing groups.

12. The method of claim 1, wherein a stabilizer is added into the polymerizable fluid composition together with the soluble silver salt, wherein the stabilizer is a polyacrylic acid (PAA), a poly(ethyleneimine) (PEI), a poly(vinylpyrrolidone) (PVP), a copolymer of acrylic acid (AA) with a vinylic monomer, acrylic acid, or polyionic material having carboxyl, amino and/or sulfur-containing groups.

13. The method of claim 1, wherein a biocompatible reducing agent is added into the mixture while mixing thoroughly the mixture so as to facilitate the formation of the polymerizable dispersion containing silver nano-particles.

14. The method claim 1, wherein the polymerizable fluid composition further comprises a pigment or a dye.

15. The method of claim 14, wherein the pigment is phthalocyanine blue, cobalt blue, Toner cyan BG, Permajet blue B2G, phthalocyanine green, chromium sesquioxide, an iron oxide, or carbazole violet, wherein the dye is a reactive blue dye.

16. The method of claim 9, wherein the biocompatible reducing agent is selected from the group consisting of ascorbic acid, biocompatible salts thereof, and salts of citrate.

17. The method of claim 13, wherein the biocompatible reducing agent is selected from the group consisting of ascorbic acid, biocompatible salts thereof, and biocompatible salts of citrate.

* * * * *